US008815499B2

(12) United States Patent
Alriksson et al.

(10) Patent No.: US 8,815,499 B2
(45) Date of Patent: *Aug. 26, 2014

(54) IN SITU DETOXIFICATION OF FERMENTATION INHIBITORS WITH REDUCING AGENTS

(75) Inventors: Björn Alriksson, Örnsköldsvik (SE); Leif Jönsson, Umeå (SE); Sune Wännström, Domsjö (SE)

(73) Assignee: Sekab E-Technology AB, Ornskoldsvik (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/517,250

(22) PCT Filed: Dec. 17, 2010

(86) PCT No.: PCT/EP2010/070132
§ 371 (c)(1),
(2), (4) Date: Oct. 10, 2012

(87) PCT Pub. No.: WO2011/080130
PCT Pub. Date: Jul. 7, 2011

(65) Prior Publication Data
US 2013/0022958 A1    Jan. 24, 2013

(30) Foreign Application Priority Data

Dec. 21, 2009 (EP) .................................... 09180194

(51) Int. Cl.
*C12Q 3/00* (2006.01)
*C12P 7/16* (2006.01)
*C12N 1/38* (2006.01)
*C12P 7/46* (2006.01)
*C12P 7/10* (2006.01)

(52) U.S. Cl.
CPC ... *C12P 7/10* (2013.01); *C12P 7/16* (2013.01); *C12N 1/38* (2013.01); *C12P 7/46* (2013.01); *C12P 2203/00* (2013.01); *Y02E 50/16* (2013.01); *Y02E 50/10* (2013.01); *Y10S 435/813* (2013.01)
USPC ................................ 435/3; 435/813; 435/243

(58) Field of Classification Search
None
See application file for complete search history.

(56) References Cited

U.S. PATENT DOCUMENTS 4,426,450 A * 1/1984 Donofrio ...................... 435/243
2006/0141587 A1* 6/2006 Kramer et al. ............... 435/108

FOREIGN PATENT DOCUMENTS

WO  WO 2007/146245 A2  12/2007
WO  WO 2009/076948 A2  6/2009

OTHER PUBLICATIONS

Jones et al., The Effect of Temperature on the Metabolism of Baker's Yeast growing on Continuous Culture, Journal of General Microbiology, 1970, vol. 60, pp. 107-116.*
Almeida, João R.M. et al., "Metabolic effects of furaldehydes and impacts on biotechnological processes", *Applied Microbiology and Biotechnology*, 2009, vol. 82, pp. 625-638.
International Preliminary Report on Patentability Corresponding to PCT/EP2010/070132; Date of Mailing: May 14, 2012; 11 Pages.
International Search Report Corresponding to International Application No. PCT/EP2010/070132; Date of Mailing: Aug. 5, 2011; 7 Pages.
Jee, H.S. et al., "Influence of Redox Potential on Biomethanation of H2 and CO2 by *Methanobacterium thermoautotrophicum* in Eh-Stat Batch Cultures", *Journal of General and Applied Microbiology*, vol. 33, 1987, pp. 401-408.
Jones, G.A. et al., "Effect of titanium (III) citrate as reducing agent on growth of rumen bacteria", *Applied Environmental Microbiology*, 1980, vol. 39(6), pp. 1144-1147.
Larsson, S. et al., "Comparison of Different Methods for the Detoxification of Lignocellulose Hydrolyzates of Spruce", *Applied Biochemistry and Biotechnology*, vol. 77-79, 1999, pp. 91-103.
Miller, E. et al., "Furfural Inhibits Growth by Limiting Sulfur Assimilation in Ethanologenic *Escherichia coli* Strain LY180", *Applied and Environmental Microbiology*, vol. 75, No. 19, Oct. 2009, pp. 6132-6141.
Olsson, L. et al., "Kinetics of Ethanol Production by Recombinant *Escherichia coli* K011", *Biotechnology and Bioengineering*, vol. 45, No. 4, 1995, pp. 356-365.
Palmqvist, E. et al., "Fermentation of lignocellulosic hydrolysates. I: Inhibition and detoxification", *Bioresource Technology*, vol. 74, Issue 1, Aug. 2000, pp. 17-24.

* cited by examiner

*Primary Examiner* — Laura Schuberg
*Assistant Examiner* — Christopher Keller
(74) *Attorney, Agent, or Firm* — Myers Bigel Sibley & Sajovec, P.A.

(57) ABSTRACT

The present invention provides a method for decreasing the fermentation inhibition in a fermentation of cellulose-derived material in a fermentor, wherein fermentation inhibitory properties of the material subjected to fermentation is decreased by an addition of at least one reducing agent to the fermentor. Further, there is provided a method of increasing the fermentability of a fermentation process comprising the steps of measuring the fermentability of the fermentation process and if the fermentability is below a reference value, then adding at least one reducing agent to the fermentation process.

5 Claims, 13 Drawing Sheets

IN SITU DETOXIFICATION OF FERMENTATION INHIBITORS WITH REDUCING AGENTS

RELATED APPLICATIONS

This application is a 35 U.S.C. §371 national phase application of PCT application PCT/EP2010/070132, filed Dec. 17, 2010, which claims priority to EP 09180194.4, filed Dec 21, 2009. The entire content of each of these applications is incorporated herein by reference.

TECHNICAL FIELD OF THE INVENTION

The present invention relates to a method for decreasing fermentation inhibitory effects of a slurry or hydrolysate during fermentation.

BACKGROUND ART

Biorefineries producing commodities from renewable resources offer an alternative to oil refineries based on dwindling supplies of petroleum and permit a move towards improved energy security. Lignocellulosic residues from forestry and agriculture are attractive as feedstocks, since they are abundant, relatively inexpensive, and are not used for food. Lignocellulose consists mainly of lignin and two classes of polysaccharides, cellulose and hemicellulose. The polysaccharides can be hydrolysed to sugars and converted to various fermentation products, such as bioalcohols, in processes based on biocatalysts, such as the industrially important baker's yeast (*Saccharomyces cerevisiae*).

The hydrolysis of cellulose is typically preceded by a pretreatment, in which the hemicellulose is degraded and the cellulose is made increasingly accessible to cellulolytic enzymes or acidic hydrolysis. However, the pretreatment process typically generates fermentation inhibitors, such as phenolic compounds, aliphatic acids, and furan aldehydes, which may have a negative effect on the efficiency of the fermentation process. Furthermore, it may be desirable to recirculate process water to achieve a cost-efficient and environmentally sound process. Such recycling of process may lead to accumulation of inhibitors that will contribute to the problems of poor fermentability.

Also, the hydrolysis itself, if performed using harsh conditions, such as low pH, high temperature and/or overpressure, may generate fermentation inhibitors.

SUMMARY OF THE INVENTION

Several methods are suggested to address inhibitor-related problems. These include choice of pretreatment conditions, design of fermentation procedure, strain selection, strain adaptation, mutation followed by selection and genetic engineering. However, manipulation of the pretreatment conditions to decrease formation of inhibitors or choosing the process design to avoid inhibitor problems can lead to decreased sugar yields, poor conversion of sugar, or poor ethanol yield and productivity. High sugar and ethanol yields and high productivity are essential for cost-efficient production of a high volume/low-value added product such as fuel ethanol Detoxification of hydrolysate, e.g. by addition of calcium hydroxide, is another suggested method. However, such alkali detoxification may result in extensive degradation of fermentable sugars. Furthermore, conventional detoxification methods generally requires extra process steps, such as steps in which the pH and/or temperature of the process stream need to be adjusted.

The inventors have realized that there is a need in the art for improved methods to overcome problems with fermentation inhibition in the manufacture of fermentation products from cellulosic material.

Therefore, it is an object of the present invention to provide a method for decreasing fermentation inhibition.

To meet this object, there is provided a method for decreasing the fermentation inhibition in a fermentation of cellulose-derived material in a fermentor, wherein fermentation inhibitory properties of the material subjected to fermentation is decreased by an addition of at least one reducing agent to the fermentor.

Further, there is provided a method of increasing the fermentability of a fermentation process comprising the steps of
a) measuring the fermentability of the fermentation process and if the fermentability is below a reference value, then
b) adding at least one reducing agent to the fermentation process.

DETAILED DESCRIPTION OF THE INVENTION

As a first aspect of the invention, there is provided a method for decreasing the fermentation inhibition in a fermentation of cellulose-derived material in a fermentor, wherein fermentation inhibitory properties of the material subjected to fermentation is decreased by an addition of at least one reducing agent to the fermentor.

Consequently, there is provided a method for decreasing the fermentation inhibition in a fermentation of cellulose-derived material in a fermentor, characterized by addition of at least one reducing agent to the fermentor for decreasing the fermentation inhibitory properties of the material subjected to fermentation.

"Fermentation" is a process known to the skilled person, and is usually performed by microorganisms in a "fermentor", which refers to any type of container or reaction vessel that may be used for preparing a target chemical by means of fermentation.

"Fermentation inhibition" refers to a negative effect on a fermentation reaction, e.g. decreasing of the rate of the fermentation reaction or the total amount of target product produced in the fermentation reaction. "Decreasing the fermentation inhibition" thus refers to decreasing such negative effects. Consequently, decreasing the fermentation inhibition may be detoxification or conditioning of a material subjected to fermentation, i.e. decreasing the effect of one or more properties of the material subjected to fermentation, which properties are inhibiting the fermenting organism's conversion of a substrate to the target chemical. For example, "decreasing the fermentation inhibition" may be increasing the saccharide consumption rate, such as the glucose consumption rate, increasing the total amount of target chemical produced during fermentation, increasing the target chemical yield on consumed saccharide during fermentation, i.e. increasing the number of target chemical molecules produced by each consumed saccharide molecule, or increasing the volumetric target chemical productivity, e.g. measured as (g target chemical$\times L^{-1} \times h^{-1}$)

"Fermentation inhibitory properties" of a material refers to any property of a material that has a negative effect on a fermentation reaction, e.g. by decreasing the turnover rate of the fermentation reaction or the total amount of target product produced in the fermentation reaction. Consequently, decreasing such properties has a positive effect on the fermentation reaction.

A "cellulose-derived material" refers to any material derived from cellulose and/or hemicellulose. For example, the "cellulose-derived material" may be a lignocellulose-derived material, such as pretreated and optionally hydrolysed lignocellulosic biomass.

A "reducing agent" refers to a chemical agent capable of causing the reduction of another substance as it itself is oxidized, i.e. a chemical agent capable of donating an electron in an oxidation-reduction reaction.

The present invention is based on the insight that the addition of a reducing agent directly to the fermentor provides for in situ detoxification and is an effective approach to overcome obstacles connected with bioconversion of cellulosic material to target chemicals. A dramatic improvement in fermentability can be achieved with a relatively small addition of reducing agent and further, the reducing agent is compatible with enzymes and fermenting organisms such as yeast, thus resulting in marginal or no influence on enzyme or yeast performance.

Further, addition of the reducing agent directly to the fermentor is advantageous, since there is no need to perform any additional separate steps for addition of the reducing agent, which could contribute to higher process costs. Thus, addition of the reducing agent directly to the fermentor permits full process flexibility, i.e. the general process design does not need to be adapted or amended for decreasing fermentation inhibition since the addition of a reducing agent is performed in the step of fermentation. The reducing agent may be added to the fermentor prior to or after a fermenting organism is added to the fermentor. Further, the reducing agent may be added concurrently with the fermenting organism.

Further, the in situ detoxification of the first aspect of the invention does not require introduction of genetically modified microorganisms in the industrial process. Further benefits of the method according to the first aspect of the invention include that the addition of the reducing agent may be carried out at a pH suitable for fermentation and at room or fermentation temperature, and results in improved fermentability without degradation of fermentable sugars. These benefits and the simplicity of the in situ detoxification according to the first aspect offer a way to achieve more efficient manufacture of fermentation products, such as ethanol, from lignocellulose hydrolysates. Consequently, the method according to the first aspect of the invention provides for an efficient production of fuels, such as ethanol, and other chemicals from cellulosic materials.

Further, the fermentation of cellulose-derived material may be performed by a fermenting organism, which refers to an organism that is capable of fermenting saccharides into a target chemical. The fermenting organism may be at least one eukaryotic or prokaryotic microorganism, such as bacteria and/or yeast. Examples of bacteria and yeasts which are capable of fermenting saccharides into other chemical compounds are known to the skilled person. Yeasts from *Saccharomyces, Pichia* and *Candida* may be used as the fermenting organism. The fermenting organism may for example be wild type, mutant or recombinant *Saccharomyces cerevisiae*. Using *S. cerevisiae* for producing a target chemical by means of fermentation is advantageous since *S. cerevisiae* is well established with regard to industrial fermentation and provides for a high product yield.

In an embodiment of the first aspect, the fermentation is a simultaneous saccharification and fermentation (SSF) of a material comprising cellulose.

A SSF process refers to a process in which enzymatic hydrolysis and fermentation is performed simultaneously in a fermentor. Enzymatic hydrolysis refers to a hydrolysis reaction catalysed by at least one enzyme. The at least one enzyme may be at least one saccharification enzyme, which refers to at least one enzyme that can convert or hydrolyse cellulosic biomass into fermentable saccharides, such as monosaccharides and/or disaccharides. Such saccharification enzymes may be glycosidases, which hydrolyse polysaccharides. Examples of glycosidases include cellulose-hydrolysing glycosidases, such as cellulases, endoglucanases, exoglucanases, cellobiohydrolases and β-glucosidases, hemicellulose hydrolysing glycosidases, such as xylanases, endoxylanases, exoxylanases, β-xylosidases, arabinoxylanases, mannanases, galactanases, pectinases and glucuronases, and starch hydrolysing glycosidases, such as amylases, α-amylases, β-amylases, glucoamylases, α-glucosidases and isoamylases, or any enzymes in the group of enzymes found in EC 3.2.1.x, such as EC 3.2.1.4, where EC is the Enzyme Commission number.

Thus, in a SSF process, fermentable saccharides are prepared directly in a fermentor by enzymatic hydrolysis of cellulose and prepared saccharides are converted by means of fermentation into a target chemical. Therefore, in an SSF-process, in which there may be a continuous turnover of fermentable saccharides by the fermenting organism, the sugar yield of the enzymatic hydrolysis reaction may be higher and build-up of high concentrations of fermentable saccharides may be prevented. High concentrations of fermentable saccharides may be inhibitory to saccharification enzymes. Moreover, a potential loss of free sugars is avoided, since the free sugars prepared by enzymatic hydrolysis in the SSF process do not need to be separated from other fractions of the cellulose-derived material before fermentation. Further, an SFF process decreases the number of vessels needed for preparing a target chemical and thereby the overall cost of the process.

Further, the fermentation may be a consolidated bioprocess (CBP), in which the biocatalyst that convert the monosaccharides also produces the enzymes that hydrolyse the cellulosic material.

In an embodiment of the first aspect, the cellulose-derived material is a hydrolysate obtained from a hydrolysis performed in a step separate from the fermentation.

In the context of the present disclosure, hydrolysis refers to subjecting the cellulosic material (i.e. material comprising cellulose and/or hemicellulose) to hydrolysing conditions such that free sugars becomes accessible in a hydrolysate for further fermentation. Consequently, hydrolysis of cellulosic material may be performed before fermentation, such that free sugars are liberated from the cellulosic material before fermentation is initiated. As an example, the cellulosic material may have been pretreated before hydrolysis. Pretreating cellulosic material refers to subjecting cellulosic material to conditions such that the cellulose becomes more accessible during subsequent hydrolysis. The pretreatment may involve one or several pretreatment methods known to the skilled man. As an example, the pretreatment may be acid pretreatment or alkali pretreatment. Further, the pretreatment may be impregnation, which refers to impregnating of the cellulosic material with an impregnation fluid, followed by heating. The fluid may be an acid solution, such as a mineral acid solution. The impregnation may also be performed with a gas, such as a $SO_2$-gas or $CO_2$-gas, or with the combination of a gas with a liquid. The pretreatment may also comprise steaming. Steaming refers to a process used to drive air out from the cellulosic biomass to facilitate further hydrolysis of the cellulose. Steaming is a well-known method for pretreating e.g. lignocellulosic biomass. As another example, the pretreatment may involve steam explosion. Steam explosion is a process that combines steam, rapid pressure releases and hydrolysis for rupturing cellulosic fibers.

As an example, the method may further comprise the step of enzymatic hydrolysis of a material comprising cellulose to obtain the hydrolysate.

Consequently, the enzymatic hydrolysis and the fermentation may be performed as two separate process steps. This may e.g. be advantageous if the fermentation reaction and the enzymatic reaction have different optimal temperatures. As an example, the temperature during enzymatic hydrolysis may be kept higher than the temperature during fermentation, thus facilitating the use of thermophilic enzymes.

Further, before enzymatic hydrolysis, the pretreated cellulosic material may be neutralized. For example, the pretreated cellulosic material may be neutralized by means of an addition of NaOH or ammonia. Also, $CaOH_2$ may be used.

As a further example, the method may further comprise the step of acidic hydrolysis of a material comprising cellulose to obtain the hydrolysate.

Acidic hydrolysis of the material comprising cellulose refers to subjecting the optionally pretreated cellulosic material to acidic conditions, such as a pH of below 4 or below 3, such that free sugars are liberated from the material. The acidic conditions may be achieved by the addition of at least one optionally diluted mineral acid, such as sulfuric acid, hydrochloric acid, nitric acid, phosphoric acid, sulfurous acid, boric acid and/or hydrofluoric acid. Further, the hydrolysis may be performed at elevated temperature and pressure. The hydrolysis may be performed in one or two steps. More than two steps is a possible option, but normally not needed. The two-step hydrolysis may be performed in two separate hydrolysis units and in two different acidic environments, which may be achieved by addition of different acids or different concentrations in the two hydrolysis units or by using different temperatures in the two separate hydrolysis units.

In an embodiment of the first aspect, the cellulose-derived material is obtained from a process of making paper pulp.

Thus, the cellulose-derived material may be process liquid from the pulping industry. Further, the process liquid may have a suspended solids content, e.g. comprise cellulose fibers. Such process liquid comprising cellulose fibers may be subjected to hydrolysis before fermentation in order to further liberate saccharides from the cellulose fibers.

Cellulose-derived material may generally be provided in large quantities from pulp making processes, and production of target chemicals by means of fermentation of cellulose-derived material obtained from such processes may be cost effective.

As an example, the cellulose-derived material may be spent cooking liquor. Spent cooking liquor refers to any process liquid from the digestion of wood during pulping. It may contain cellulose-derived material and other wood chemicals, such as lignin, and spent digestant, depending on the pulping process used.

Further, the cellulose-derived material may be process liquid from sulphite pulping of cellulosic material. Sulphite pulping refers to the process of producing pulp form lignocellulosic material by using various salts of sulfurous acid to extract lignin. Process liquid from sulphite pulping generally comprises hemicellulose-derived monosaccharides and may thus be subjected to fermentation.

In an embodiment of the first aspect, the at least one reducing agent is added to a material having a temperature of 28-38° C.

Thus, the reducing agent may be added as the material subjected to fermentation has a temperature of 28-38° C., which means that the reducing agent may be added at a temperature suitable for fermentation. Therefore, extra process steps for adjusting the temperature may not be required.

Preliminary results indicate that detoxification with reducing agents may be performed at various pH levels. The inventors have however noted that the detoxification with reducing agents appears to be more efficient at a pH above 3, such as above 4, than at a pH below 3, such as below 2.5. This means that the inventors believe that the detoxification is more efficient if it is performed after pretreated material or hydrolysed material, which often has a pH of around 2, is neutralized.

Thus, in an embodiment of the first aspect, the at least one reducing agent is added to a material having a pH of 3-7, such as 4-6, such as 5-6.

This means that the reducing agent may be added at a pH that is suitable for hydrolysis and/or fermentation. For example, fermentation and SSF is often performed at a pH of about 5.5. Extra process steps for adjusting the pH may therefore not be required.

In an embodiment of the first aspect, the cellulose-derived material is lignocellulose-derived material.

Lignocellulose-derived material refers to material obtainable from lignocellulosic material, which comprises cellulose, lignin and possibly hemicellulose. The lignocellulose-derived material may for example be derived from wood residues or forestry residues, such as wood chips, sawmill or paper mill discards, or agricultural residues. As an example, the lignocellulose-derived material may be wood-derived material or sugarcane bagass-derived material. Depending on the geographical location, wood or sugarcane bagass may be available in large quantities, making them attractive as raw materials. The lignocellulose-derived material may for example be hydrolysates of wood or sugarcane bagass.

In an embodiment of the first aspect, the at least one reducing agent comprises sulphur. As an example, the at least one reducing agent may be selected from dithionite and sulphite. These reducing agents have shown to be suitable for decreasing the fermentation inhibition as shown in the Examples of the present disclosure. Sulphite ($SO_3^{2-}$) is used in several large-scale industrial processes. Dithionite ($S_2O_4^{2-}$) is an industrial chemical used in the pulp and paper industry for reductive bleaching and in the textile industry as a reducing agent in dyeing processes. Hence, both sulphite and dithionite are available in large quantities. Further, it is to be understood the reducing agent may comprise sulphite and/or dithionite in salt form, i.e. complexed with different cations. Examples include $Na_2SO_3$, $NaHSO_3$, $KHSO_3$, and $Na_2S_2O_4$.

As an example, the reducing agent may be dithionite and the dithionite may be added in an amount such that the concentration of dithionite during fermentation is 1-30 mM, such as 5-25 mM, such as 7.5-20 mM. As a further example, the reducing agent is sulphite and the sulphite is added in an amount such that the concentration of sulphite during fermentation is above 10 mM, such as above 15 mM, such as above 20 mM.

These concentrations of dithionite and sulphite, respectively, have shown to be suitable for decreasing fermentation inhibition, as shown in the Examples of the present disclosure. It may however be disadvantageous for the fermentation process to add more than 100 mM of sulphite. Thus, the amounts of dithionite or sulphite required to achieve a decrease in fermentation inhibitory properties are relatively low and the results from Examples of the present disclosure show that such amounts of dithionite or sulphite permit production of high levels of ethanol using e.g. SSF procedures. Further, it may be more advantageous to add dithionite compared sulphite, since addition of dithionite results in a larger decrease in fermentation inhibition compared to sulphite when added to the same concentration, as seen in the Examples of the present disclosure. Consequently, the same fermentation inhibitory effect may be achieved by addition of a lower concentration of dithionite compared to sulphite. Addition of a lower concentration of dithionite compared to sulphite also means that the total salt concentration during fermentation is lower, which may be beneficial for the fermentation reaction.

Other compounds that may be used as reducing agents include thiosulphates ($S_2O_3^{2-}$), such as $Na_2S_2O_3 \cdot 5H_2O$ and $Na_2S_2O_3$, alkali-decomposed sugars, ascorbic acid, cysteine, diethanolamine, triethanolamine, dithiothreitol (DTT) and reduced glutathione.

In embodiments of the invention, ethanol is produced in the fermentation of the cellulose-derived material. Ethanol is a target chemical that is derivable from cellulosic biomass and which can be produced by means of fermentation. The target chemical may also be butanol or succinic acids, which are also derivable from cellulosic material. Other examples of target chemicals are other alcohols or acids, alkanes, alkenes, aromatics, aldehydes, ketones, biopolymers, proteins, peptides, amino acids, vitamins, antibiotics and other pharmaceuticals.

In an embodiment of the first aspect of the invention, the material to which the reducing agent is added has a suspended solids content of at least 5% (w/w), such as at least 10% (w/w), such as at least 12% (w/w).

It has been found that the reducing agent may be added to a cellulosic material having relatively high solids content, such as the cellulosic material subjected to SSF or CBP. This enables detoxification or conditioning of pretreated slurry of cellulosic material without any solids separation step. Such in situ detoxification or conditioning provides for a high product yield and cost-efficient recovery of the target chemical, for example through distillation.

In an embodiment of the first aspect of the invention, the material to which the reducing agent is added has a sugar concentration of at least 45 g/l, such as at least 65 g/l, such as at least 85 g/l.

Consequently, the reducing agent may be added to a cellulose-derived material having a high sugar concentration, such as to hydrolysed cellulosic material.

In the context of the present disclosure, "sugars" refers to fermentable saccharides, such as a fermentable monosaccharides and disaccharides.

In embodiments of the invention, the method according to the first aspect of the invention is further comprising measuring the fermentability of the fermentation of hydrolysed material; and if the measured fermentability is below a reference value, adding at least one reducing agent to the fermentation.

In the context of the present disclosure, the "fermentability" of a fermentation is any parameter that is proportional to the result of the fermentation process. As examples, the fermentability may be the sugar consumption rate, the amount of produced target chemical, the produced target chemical yield on consumed sugars and/or the volumetric target chemical productivity.

The sugar consumption rate may be measured as the decrease of sugar concentration per hour, the amount of target chemical may be measured as g target chemical per liter, the produced target chemical yield on consumed sugars may be measured as the number of target chemical molecules produced by each consumed saccharide molecule by monitoring the decrease in saccharide concentration and the increase of target chemical concentration during fermentation, and the volumetric target chemical productivity may be measured as g target chemical per liter and hour. Further, the fermentability may be measured by measuring the total sugar concentration. If for example the fermenting organism becomes less effective in a SSF process, an increase of total sugar concentration may be measured. Thus, the fermentability may also be the inverse value of the total sugar concentration.

Thus, it has further come to the inventor's insight that, in the process for producing a target chemical from cellulosic biomass, an addition of at least one reducing agent to a fermentation process having a low fermentability may increase the fermentability of that process. Hence, this offers the possibility of "rescuing" a fermentation process that in some way does not function properly. As an example, the glucose consumption rate may be continuously monitored in a fermentation process and if the rate is below a satisfactory reference level, a reducing agent may be added in order to increase the glucose consumption rate. The reference value of the fermentability may for example be selected such that a fermentation process having a fermentability below the reference value, such as below a certain glucose consumption rate, leads to an unsatisfactory amount of target chemical, and a fermentation process having a fermentability above the reference value, such as above a certain glucose consumption rate, leads to a desired amount of target chemical. Given the teachings of the present disclosure, the skilled person understands how to select a reference value for the fermentability.

It is shown in the Example referring to FIG. 8 below that the fermentation capacity in a fermentation that has been subjected to the inhibitors for a longer time may not completely recover even though the reducing agent is added. Without being bound by any scientific theory, the inventors believe that this may be due to that part of the yeast dies. Thus, in cases of insufficient fermentability in an ongoing fermentation or SSF, extra yeast may be added in addition the reducing agent. The extra yeast may be added before, concurrently or after the reducing agent. For example, the yeast and the reducing agent may be added within two hours, such as within one hour or 30 minutes.

In processes for producing a target chemical by means of fermentation, recirculation of process water generally leads to an accumulation of the inhibitory properties of the process water. However, since the addition of a reducing agent according to the first aspect of the invention decreases the fermentation inhibition, recirculation of process water may be performed without any detrimental accumulation of inhibitory properties. Therefore, in embodiments of the first aspect, the method is further comprising recirculating, optionally after purification, at least part of the water obtained from the production of the target chemical to at least one of the steps in the production of the target chemical.

Recirculation process water refers to reusing process water upstream in the process for producing a target chemical. As an example, part or all of the fermentation broth may be recirculated. Further, if the target chemical is extracted from the fermentation broth by means of distillation, part or all of the stillage (e.g. a filtrate of the stillage) may be recirculated. The recirculated process water may for example be used as a pretreatment fluid in a pretreatment of cellulosic material, as a hydrolysing liquid in a hydrolysis of cellulosic material or as a fermentation liquid in a fermentation of sugars.

Consequently, recirculation of process water decreases the need of introducing fresh water in the production of target chemicals from cellulosic biomass.

In a second aspect of the invention, there is provided a method of increasing the fermentability of a fermentation process comprising the steps of
 a) measuring the fermentability of the fermentation process and if the fermentability is below a reference value, then
 b) adding at least one reducing agent to the fermentation process.

The terms and definitions used in the second aspect of the invention are as defined in connection with the first aspect above. Further, the embodiments of the first aspect apply mutatis mutandis to the second aspect. The second aspect of the invention is based on the insight that addition of a reducing agent to a fermentation process in which the fermentability is low may increase the fermentability of that process. Thus, this offers the possibility of "rescuing" a fermentation process that in some way does not function properly. As examples, the fermentability may be the sugar consumption rate, the amount of produced target chemical, the produced target chemical yield on consumed sugars and/or the volumetric target chemical productivity. As described above, the fermentability may also be the inverse value of the total sugar concentration. Given the teachings of the present disclosure, the skilled person understands how to select a reference value for the fermentability.

EXAMPLES

Figure 1:
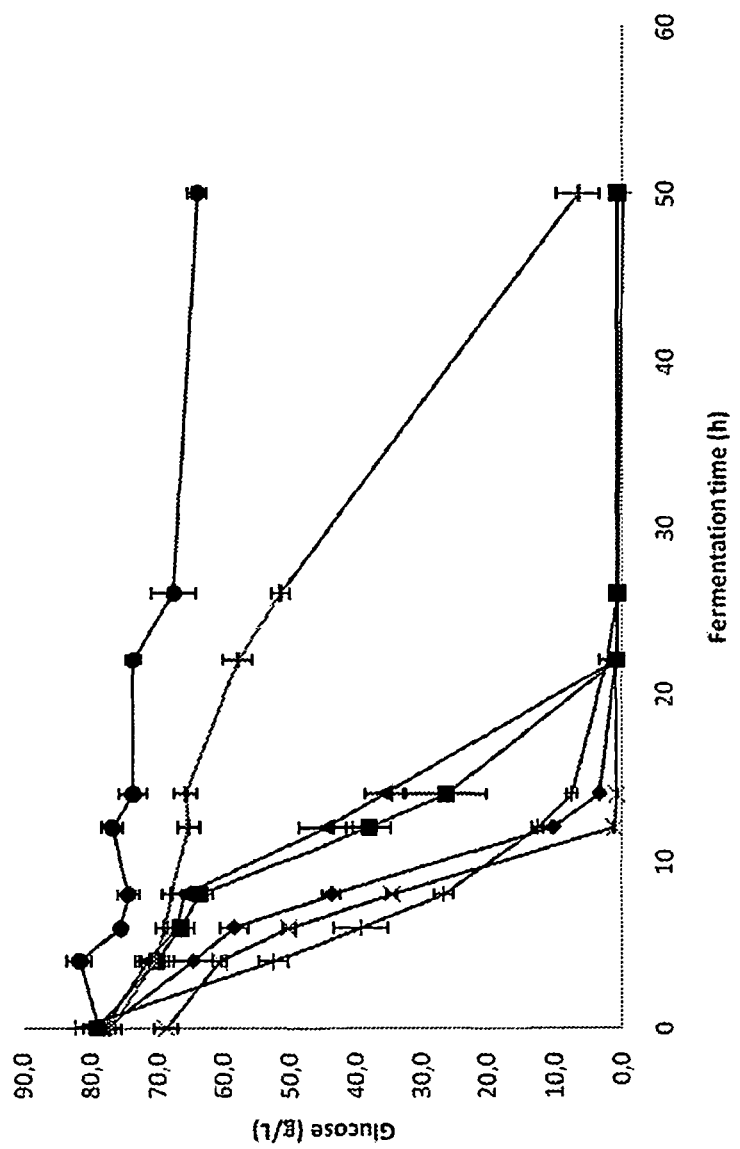
FIG. 1 shows the glucose consumption in the experiment with separate hydrolysis and fermentation of a spruce hydrolysate. Every point in the graph is calculated as the mean value of two fermentations. The error bars indicate the standard deviations. The data indicate: ■: dithionite addition (5 mM), ♦: dithionite addition (10 mM), –: sulphite addition (5 mM), ▲: sulphite addition (10.0 mM), ●: untreated hydrolysate, ×: NH$_4$OH treatment and +: reference fermentation.

The following non-limiting examples will further illustrate the present invention.

Example 1

Control Experiment

Effect of Sulphite and Dithionite on Saccharide Concentrations of a Hydrolysate Prepared by Enzymatic Hydrolysis Materials and Methods Lignocellulose hydrolysates were produced from spruce wood and sugarcane bagass through thermochemical pretreatment and subsequent enzymatic hydrolysis.

For SHF experiments with sugarcane bagass, one kg (dry weight, DW) of dried sugarcane bagass was impregnated with 500 g of dilute sulfuric acid (4%) and kept in a plastic bag for 20 h. The impregnated sugarcane bagass was then loaded into a 30-liter reactor. The material was treated with steam at a temperature of 195° C. and a pressure of 14.1 bar during 15 min. The pretreated material, hereafter referred to as the sugarcane bagass slurry, was cooled and stored at 4° C. until further use.

The pretreatment of spruce was performed by SEKAB E-Technology in the Swedish cellulosic ethanol pilot plant (operated by SEKAB, Örnsköldsvik, Sweden). Unbarked wood chips were treated in a continuous mode with sulfur dioxide in a 30-litre reactor at a temperature of 203° C., at a pH of 2.0-2.3, and with a residence time of 5 min. One kg of sulfur dioxide per 40 kg of wood chips was used, and the dry matter content was 25-27%. The pretreated material, hereafter referred to as the spruce slurry, was cooled and stored at 4° C. until further use.

The pretreatment of sugarcane bagass for SSF experiments was performed in the Swedish cellulosic ethanol pilot plant (operated by SEKAB E-Technology, Örnsköldsvik, Sweden). Sugarcane bagass was treated in a continuous mode in a 30-litre reactor at a temperature of 198-199° C. and with a residence time of 13-14 min. The feed rate was 24 kg (dry weight) per h and the sugarcane bagass was impregnated with sulfur dioxide (0.5 kg/h). The pH after pretreatment was 2.7. The dry matter content was 19%. The pretreated material was cooled and stored at 4° C. until further use.

The pH of the sugarcane bagass slurry was adjusted to 5.3 with a 5 M solution of sodium hydroxide. The slurry was then filtered and part of the liquid fraction was discarded to give the slurry a dry-matter content of 10%. Four 2-L shake flasks were filled with 750 g of slurry. The pH of the spruce slurry was adjusted to 5.3 with a 5 M solution of sodium hydroxide. Six 750-mL shake flasks were filled with 350 g of slurry. The dry-matter content was 16%.

Commercially available preparations of cellulase and cellobiase were added to the slurries. The cellulase preparation, which was from *Trichoderma reesei* ATCC 26921, had a stated activity of 700 endoglucanase units (EGU)/g (Sigma-Aldrich, Steinheim, Germany) and the loading was 319 EGU/g of solids (DW). The cellobiase preparation, Novozyme 188, had a stated activity of 250 cellobiase units (CBU)/g (Sigma-Aldrich) and the loading was 23 CBU/g of solids (DW). The enzyme dosages were based on the results of a set of small-scale experiments. After addition of enzymes, the slurries were incubated with shaking (Infors Ecotron, Infors AG, Bottmingen, Switzerland) at 50° C. and 70 rpm for 48 h.

After the hydrolysis, the slurries were filtered and the amounts of released glucose and mannose in the slurries were measured by high-performance liquid chromatography (HPLC). The pH of the liquid fractions, hereafter referred to as sugarcane bagass and spruce hydrolysate, was adjusted to pH 2.0 with a 12 M solution of hydrochloric acid to prevent microbial growth during storage. The sugarcane bagass hydrolysate was concentrated by evaporation (Rotavapor Büchi 001, Büchi Labortechnik AG, Flawil, Switzerland) to obtain a similar glucose concentration as in the spruce hydrolysate. The hydrolysates were stored at 4° C. until further use.

The pH of the sugarcane bagass and spruce hydrolysates were adjusted to 5.5 with a 5 M solution of sodium hydroxide. The conditioning of each hydrolysate was performed in eight 100-mL glass vessels equipped with magnetic stirrer bars. 26 mL hydrolysate was added to all vessels, and the vessels were placed on a magnetic stirrer plate (IKA-Werke, Staufen, Germany). Sodium dithionite (chemical grade; >87%, Merck, Darmstadt, Germany) was added to hydrolysates in the concentrations 5 and 10 mM. Additions of sodium sulphite to 5 and 10 mM were also performed. The additions were made at room temperature (23° C.) and the samples were kept for 10 min with stirring. The experiments were performed in duplicates.

The efficiency of the additions of the reducing agents was compared with alkali detoxification. Therefore, a hydrolysate sample was treated with ammonium hydroxide under conditions previously described (Alriksson et al. (2006), *Appl. Biochem. Biotechnol.* 129-132, 599-611.) The pH was adjusted to 9 and the hydrolysate was kept at 55° C. for 3 h with stirring.

Analyses of monosaccharides and furan aldehydes [furfural and 2-hydroxymethylfurfural (HMF)] were performed by using high-performance liquid chromatography (HPLC). A Shodex SH-1011 column (6 μm, 8×300 mm) (Showa Denko, Kawasaki, Japan) was used in a YoungLin YL9100 series system (YoungLin, Anyang, Korea) equipped with a YL9170 series refractive index (RI) detector for analysis of glucose, mannose, galactose, HMF, and furfural. Elution was performed with isocratic flow of a 0.01M aqueous solution of $H_2SO_4$. The flow rate was 1.0 mL/min and the column temperature was set to 50° C. For analysis of xylose and arabinose, a Shodex SP-0810 column (7 μm, 8×300 mm) was used with the same HPLC system. The elution was performed using Milli-Q water at a flow rate of 1.0 mL/min and the column temperature was set to 80° C. YLClarity software (YoungLin, Anyang, Korea) was used for data analysis.

Determination of the total amount of phenolic compounds was performed using HPLC (MoRe Research, Örnsköldsvik, Sweden) according to a previously described method (Nilvebrant et al. (2001) *Appl. Biochem. Biotechnol.* 91-93, 35-49).

Ethanol measurements were performed by using an enzymatic kit (Ethanol UV-method, Boehringer Mannheim GmbH, Mannheim, Germany). Fermentation experiments were performed to evaluate the effectiveness of the additions and treatments. For comparison, untreated hydrolysates were included in the fermentation experiments as well as reference fermentations of sugar-based medium with an amount of fermentable sugars (i.e. glucose and mannose) corresponding to that in the hydrolysate samples. The fermentations were carried out using baker's yeast (*Saccharomyces cerevisiae*) (Jästbolaget AB, Rotebro, Sweden). The yeast inoculum was prepared in 750-mL cotton-plugged shake flasks with 300 mL YEPD medium (2% yeast extract, 1% peptone, 2% D-glucose). The flasks were inoculated and incubated with agitation at 30° C. for approximately 12 h. The cells were harvested in the late exponential growth phase by centrifugation (Hermla Z206A, Hermle Labortechnik GmbH, Wehingen, Germany) at 1,500 g for 5 min. The cells were resuspended in an appropriate amount of sterile water to achieve an inoculum consisting of 2.0 g/L (cell dry weight) in all fermentation vessels. The fermentation was carried out in 14 25-mL glass flasks equipped with magnets for stirring and sealed with rubber plugs pierced with cannulas for letting out carbon dioxide. The hydrolysate samples (23.75 mL), or alternatively the sugar solution for reference fermentations, were added to the fermentation flasks along with 0.5 mL of a nutrient solution (150 g/L yeast extract, 75 g/L $(NH_4)_2HPO_4$, 3.75 g/L $MgSO_4.7H_2O$, 238.2 g/L $NaH_2PO_4.H_2O$), and 0.75 mL of yeast inoculum. The flasks were incubated at 30° C. in a water bath with magnetic stirring (IKA-Werke). Samples for measurement of sugars and ethanol were withdrawn during the fermentation. The glucose levels during the fermentation were estimated by using a glucometer (Glucometer Elite XL, Bayer AG, Leverkusen, Germany).

Results

The preparation of spruce and sugarcane bagasse hydrolysates for SHF experiments resulted in hydrolysates with over 80 g/L glucose and more than 100 g/L of monosaccharides (Tables 1 and 2). Glucose was the predominant fermentable sugar in both hydrolysates, but the spruce hydrolysate contained, as expected, large amounts of mannose (Table 1). The total concentrations of phenolic compounds, as estimated by HPLC, were relatively similar. Both hydrolysates contained about four g/L furan aldehydes and about three times as much HMF as furfural. The contents of aliphatic acids were slightly higher in the spruce hydrolysate than in the sugarcane bagasse hydrolysate. In both cases, acetic acid was most common among the aliphatic acids.

The concentrations of monosaccharides were not affected by the additions of dithionite or sulphite (Tables 1 and 2). However, the alkali detoxification, i.e. the addition of $NH_4OH$, resulted in lower sugar concentrations compared to addition of dithionite or sulphite. For example, the glucose concentration of the spruce hydrolysate after alkali detoxification was only about 70 g/L, whereas addition of dithionite or sulphite led to glucose concentrations above 80 g/L. Alkali detoxification also led to smaller amounts of xylose, galactose and mannose in the spruce hydrolysate compared to when dithionite or sulphite were used. Further, alkali detoxification led to smaller amounts of xylose and galactose in the bagasse hydrolysate compared to when dithionite or sulphite were added (Tables 1 and 2). Consequently, addition of dithionite and sulphite resulted in higher sugar concentrations compared to alkali detoxification.

TABLE 1

Concentrations (g/L) of monosaccharides and inhibitors in the spruce hydrolysate used for experiments with separate hydrolysis and fermentation.

| | Glucose | Xylose | Galact | Mannose | Arabin. | Phen. | Furfural | HMF | Acetic acid | Levulinic acid | Formic acid |
|---|---|---|---|---|---|---|---|---|---|---|---|
| Untreat. hydro. | 82.9 ± 4.7 | 9.1 ± 0.1 | 3.7 ± 0.1 | 26.4 ± 0.5 | 2.8 ± 0.1 | 0.38 ± 0.01 | 1.2 ± 0.1 | 3.2 ± 0.1 | 4.7 ± 0.3 | 0.2 ± 0.1 | 0.6 ± 0.1 |
| Dithionite (5 mM) | 83.3 ± 1.2 | 9.2 ± 0.1 | 3.9 ± 0.4 | 26.5 ± 0.1 | 3.0 ± 0.1 | 0.42 ± 0.01 | 0.9 ± 0.1 | 3.4 ± 0.1 | 5.2 ± 0.1 | 0.2 ± 0.1 | 0.7 ± 0.1 |
| Dithionite (10 mM) | 82.4 ± 2.9 | 9.2 ± 0.1 | 3.8 ± 0.3 | 26.4 ± 0.7 | 2.9 ± 0.2 | 0.44 ± 0.05 | 1.0 ± 0.1 | 3.3 ± 0.2 | 5.0 ± 0.4 | 0.2 ± 0.1 | 0.7 ± 0.1 |
| Sulphite (5 mM) | 81.1 ± 0.8 | 9.1 ± 0.1 | 3.9 ± 0.1 | 26.2 ± 0.3 | 3.0 ± 0.2 | 0.43 ± 0.02 | 1.0 ± 0.1 | 3.4 ± 0.1 | 4.7 ± 0.2 | 0.2 ± 0.1 | 0.6 ± 0.1 |
| Sulphite (10 mM) | 82.4 ± 0.2 | 9.2 ± 0.1 | 3.8 ± 0.4 | 26.4 ± 0.7 | 2.9 ± 0.1 | 0.39 ± 0.03 | 1.0 ± 0.1 | 3.4 ± 0.1 | 5.1 ± 0.3 | 0.2 ± 0.1 | 0.7 ± 0.1 |
| $NH_4OH$-detox. | 72.4 ± 5.5 | 8.2 ± 0.1 | 3.3 ± 0.1 | 23.3 ± 0.7 | 2.8 ± 0.2 | 0.39 ± 0.03 | 0.7 ± 0.1 | 1.7 ± 0.1 | 4.7 ± 0.2 | 0.2 ± 0.1 | 0.7 ± 0.1 |

Abbreviations used:
Galact = galactose;
Arabin = arabinose;
Phen = phenolic compounds;
HMF = 2-hydroxymethylfurfural;
Untreat. hydro = untreated hydrolysate;
$NH_4OH$-detox. = ammonium hydroxide detoxification.

TABLE 2

Concentrations (g/L) of monosaccharides and inhibitors in the sugarcane bagasse hydrolysate used for experiments with separate hydrolysis and fermentation.

| | Glucose | Xylose | Galact | Mannose | Arabin. | Phen. | Furfural | HMF | Acetic acid | Levulinic acid | Formic acid |
|---|---|---|---|---|---|---|---|---|---|---|---|
| Untreat. hydro. | 86.3 ± 0.9 | 14.1 ± 0.1 | 9.8 ± 0.1 | 0.5 ± 0.1 | 0.2 ± 0.1 | 0.58 ± 0.03 | 1.0 ± 0.1 | 3.0 ± 0.2 | 3.2 ± 0.1 | 0.2 ± 0.1 | 0.6 ± 0.1 |
| Dithionite (5 mM) | 85.3 ± 0.6 | 14.5 ± 0.3 | 9.4 ± 0.1 | 0.4 ± 0.1 | 0.2 ± 0.1 | 0.62 ± 0.01 | 0.9 ± 0.1 | 3.0 ± 0.1 | 3.4 ± 0.1 | 0.3 ± 0.1 | 0.7 ± 0.1 |
| Dithionite (10 mM) | 85.8 ± 0.4 | 14.3 ± 0.7 | 9.5 ± 0.4 | 0.3 ± 0.1 | 0.3 ± 0.1 | 0.54 ± 0.06 | 0.9 ± 0.1 | 3.0 ± 0.1 | 3.6 ± 0.3 | 0.3 ± 0.1 | 0.8 ± 0.1 |
| Sulphite (5 mM) | 85.0 ± 0.2 | 14.1 ± 0.3 | 9.6 ± 0.7 | 0.3 ± 0.1 | 0.2 ± 0.1 | 0.56 ± 0.04 | 1.0 ± 0.1 | 2.9 ± 0.1 | 3.1 ± 0.4 | 0.3 ± 0.1 | 0.7 ± 0.1 |
| Sulphite (10 mM) | 85.6 ± 0.2 | 14.3 ± 0.1 | 9.6 ± 0.1 | 0.4 ± 0.1 | 0.2 ± 0.1 | 0.63 ± 0.01 | 1.0 ± 0.1 | 3.0 ± 0.1 | 3.3 ± 0.1 | 0.3 ± 0.1 | 0.7 ± 0.1 |

TABLE 2-continued

Concentrations (g/L) of monosaccharides and inhibitors in the sugarcane bagass hydrolysate used for experiments with separate hydrolysis and fermentation.

| | Glucose | Xylose | Galact | Mannose | Arabin. | Phen. | Furfural | HMF | Acetic acid | Levulinic acid | Formic acid |
|---|---|---|---|---|---|---|---|---|---|---|---|
| NH$_4$OH-detox. | 85.8 ± 0.4 | 12.6 ± 0.2 | 8.6 ± 0.1 | 0.3 ± 0.1 | 0.2 ± 0.1 | 0.60 ± 0.01 | 0.6 ± 0.1 | 1.6 ± 0.1 | 3.2 ± 0.1 | 0.2 ± 0.1 | 0.7 ± 0.1 |

Abbreviations used:
Galact = galactose;
Arabin = arabinose;
Phen = phenolic compounds;
HMF = 2-hydroxymethylfurfural;
Untreat. hydro = untreated hydrolysate;
NH$_4$OH-detox. = ammonium hydroxide detoxification.

Figure 2:
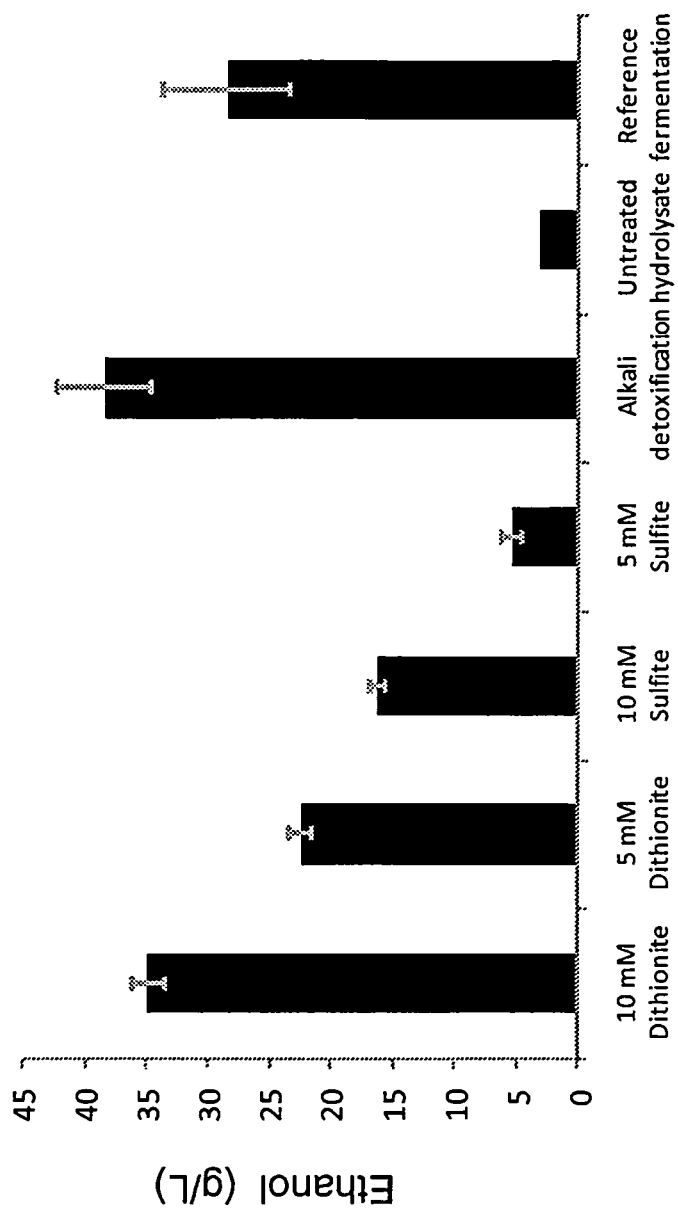
FIG. 2 shows the ethanol production (g/L) after 14 h fermentation of the spruce hydrolysate (separate hydrolysis and fermentation experiment). Every bar is calculated as the mean value of two fermentations. The error bars indicate the standard deviations.

Only a very small fraction of the glucose was consumed in untreated spruce hydrolysate even after 50 h of fermentation, which shows that the spruce hydrolysate was very inhibitory (FIG. 1). The glucose consumption rates (FIG. 1) and the amounts of ethanol produced (FIG. 2) in spruce hydrolysate with 10 mM dithionite were comparable to those of the reference fermentation. The samples with 5 mM dithionite or 10 mM sulphite showed a substantial improvement compared to untreated hydrolysate (FIGS. 1 and 2).

Figure 3:
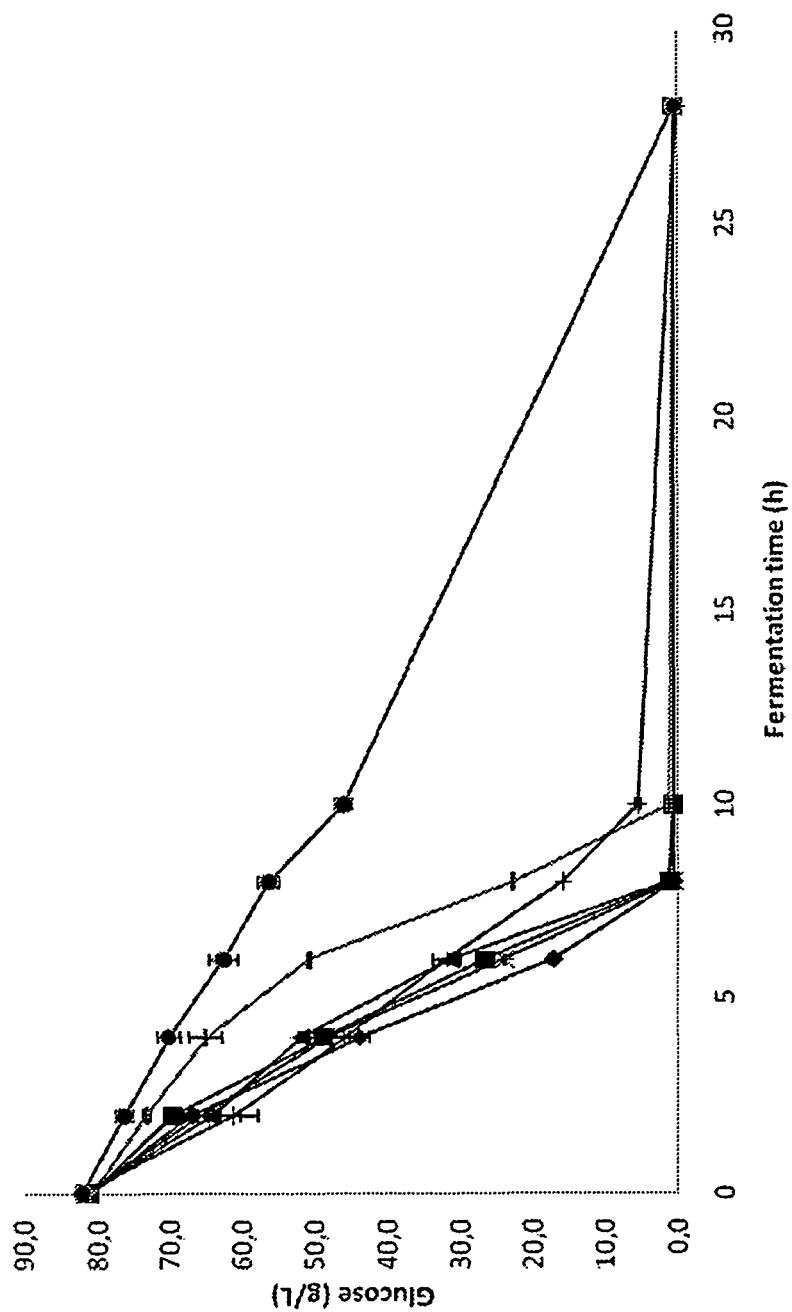
FIG. 3 shows the glucose consumption in the experiment with separate hydrolysis and fermentation of the sugarcane bagass hydrolysate. Every point in the graph is calculated as the mean value of two fermentations. The error bars indicate the standard deviations. The data indicate: ■: dithionite treatment (5 mM), ♦: dithionite treatment (10.0 mM), –: sulphite (5 mM). ▲: sulphite treatment (10.0 mM), ●: untreated hydrolysate, ×: NH$_4$OH treatment and +: reference fermentation.

The sugarcane bagass hydrolysate was not as inhibitory as the spruce hydrolysate, since there was a steady consumption of glucose, which was depleted in the sample taken after 28 h of fermentation (FIG. 3). The differences between the effects of the various treatments were therefore less pronounced in the bagass hydrolysates, but they follow the same pattern as observed in the spruce hydrolysate.

Figure 4:
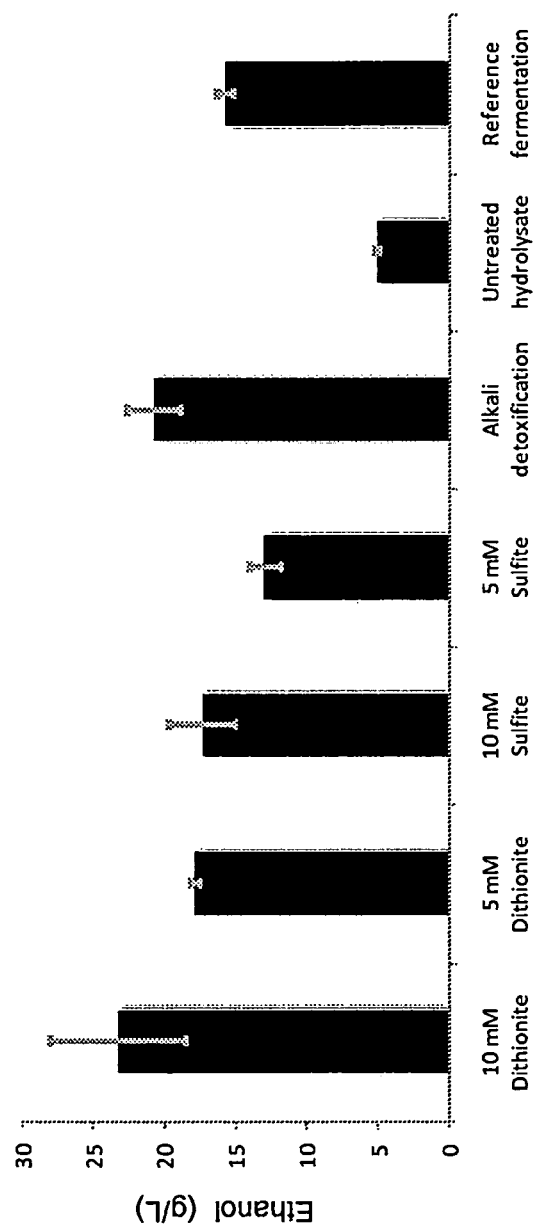
FIG. 4 shows the ethanol production (g/L) after 6 h fermentation of the sugarcane bagass hydrolysate (separate hydrolysis and fermentation). Every bar is calculated as the mean value of two fermentations. The error bars indicate the standard deviations.

Addition of dithionite or sulphite also resulted in high ethanol production from bagass hydrolysate, as seen in FIG. 4. Addition of 10 mM dithionite and resulted in a higher ethanol concentration compared to addition of 5 mM dithionite or 10 mM sulphite.

The ethanol yields on consumed sugars (Table 3) were improved by addition of dithionite or sulphite. For dithionite addition, the ethanol yields were even higher than in the reference fermentations (Table 3). The ethanol yield was comparable to those found using the alkali detoxification.

TABLE 3

Ethanol yield and productivity in experiments with separate hydrolysis and fermentation. The table shows the values obtained after 14 h (spruce hydrolysate) and 6 h (bagass hydrolysate) fermentation.

| | Yield | | Productivity | | Balanced ethanol yield | |
|---|---|---|---|---|---|---|
| | Spruce hydro. | Bagass hydro. | Spruce hydro. | Bagass hydro. | Spruce Hydro. | Bagass Hydro. |
| Untreated hydro. | 0.21 | 0.21 | 0.2 | 0.9 | 0.03 | 0.06 |
| Dithionite (10 mM) | 0.37 | 0.34 | 2.5 | 3.9 | 0.34 | 0.28 |
| Sulphite (10 mM) | 0.29 | 0.32 | 1.2 | 2.9 | 0.16 | 0.21 |
| NH$_4$OH detox. | 0.43 | 0.34 | 2.8 | 3.5 | 0.37 | 0.25 |
| Ref. ferment. | 0.33 | 0.29 | 2.0 | 2.6 | 0.28 | 0.19 |

Abbreviations used:
spruce hydro. = spruce hydrolysate;
bagass hydro. = bagass hydrolysate;
untreated hydro. = untreated hydrolysate;
NH$_4$OH detox. = NH$_4$OH detoxification;
Ref. Ferment = reference fermentation.
Yield is expressed as g EtOH/g consumed glucose & mannose.
Productivity is expressed as (g EtOH × L$^{-1}$ × h$^{-1}$).
Balanced ethanol yield is expressed as g EtOH/Σglucose & mannose prior to detoxification.

Further, the volumetric ethanol productivities for samples treated by addition of dithionite or by ammonium hydroxide detoxification rose significantly and were higher than the corresponding values for the reference fermentation (Table 3).

Consequently, addition of dithionite or sulphite resulted in ethanol yields that were in line with or higher than the yield of the reference fermentation. Moreover, dithionite addition also resulted in an ethanol productivity that was higher than the reference fermentation.

Thus, Example 1 shows that the addition of reducing agents to spruce and bagass hydrolysates does not result in reduced sugar levels, thus demonstrating that reducing agents are suitable for chemical in situ detoxification. Further, Example 1 also shows that the addition of reducing agents to a hydrolysate also provides for the subsequent production of ethanol by means of fermentation.

Example 2

Detoxification of Hydrolysate (Prepared by Enzymatic Hydrolysis) in a Simultaneous Saccharification and Fermentation (SSF) Process Materials and Methods Addition of sodium dithionite and sodium sulphite was tested in an SSF process. Spruce was pretreated as described in Example 1 above. The spruce slurry was adjusted to pH 5.4 with a 5 M solution of sodium hydroxide. Ten 250-mL shake flasks equipped with magnetic stirrer bars were filled with 100 g of spruce slurry. Sodium dithionite or sodium sulphite was added to the slurries to final concentrations of 7.5 and 10 mM. The additions were performed at room temperature (23° C.) for 10 min with stirring. Duplicate experiments were made. Cellulase and cellobiase preparations were prepared and added to the slurry using the enzyme activity loadings as described in Example 1 above. Further, the yeast inoculum was prepared according to Example 1 above. Inoculums were added to give a start concentration of 2.0 g/L (cell dry weight) in every flask. No source of extra nutrients was added. For comparison, two flasks with spruce slurry to which no reducing agents had been added were included in the experiment. The flasks were incubated at 35° C. for 69 h in a water bath with magnetic stirring. The flasks were sealed with Parafilm (Pechiney Plastic Packaging Company, Chicago, Ill., USA) to prevent evaporation of ethanol. Samples were withdrawn for analysis of ethanol according to Example 1 above.

Results

Figure 5:
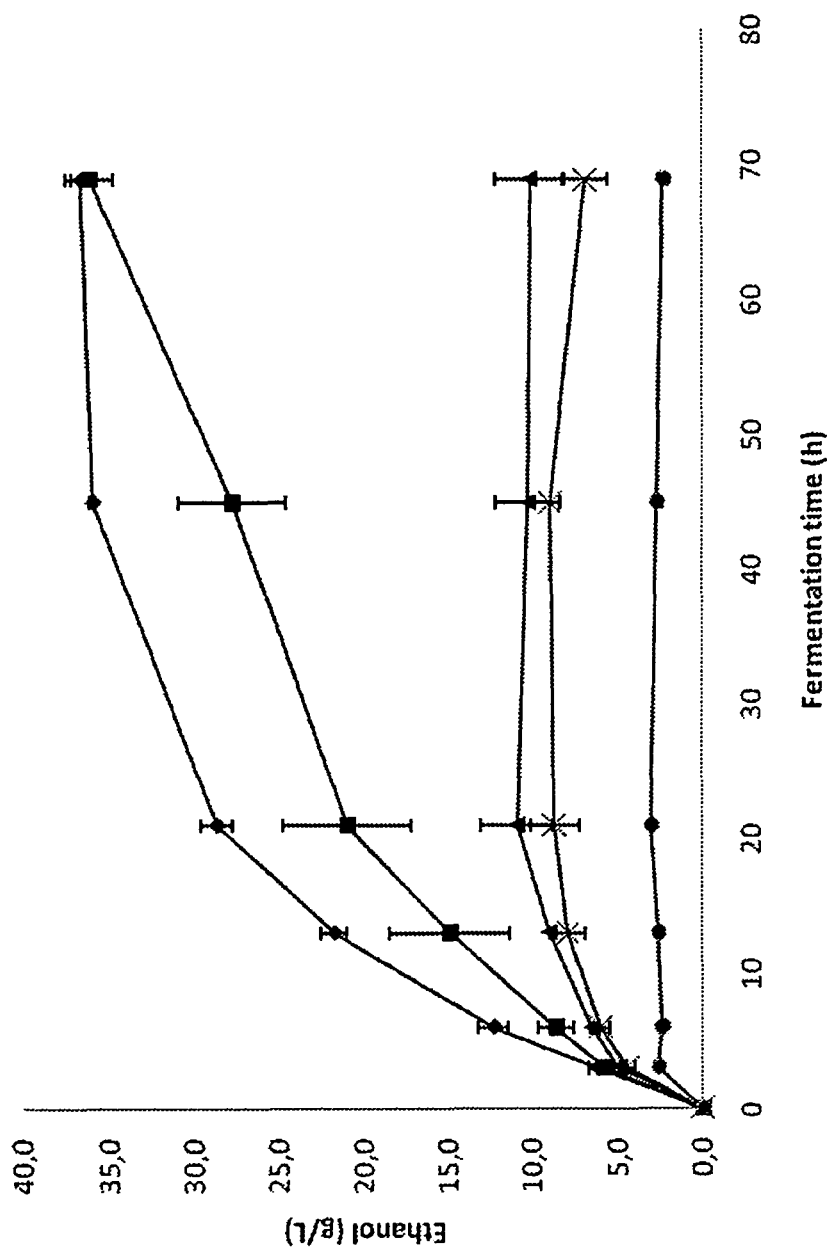
FIG. 5 shows the ethanol production during simultaneous saccharification and fermentation of spruce slurry. Every point in the graph was calculated as the mean value of two fermentations. The error bars indicate the standard deviations. The data indicate: ■: dithionite treatment (7.5 mM), ♦: dithionite treatment (10 mM), ×: sulphite treatment (7.5 mM), ▲: sulphite treatment (10 mM) and ●: untreated slurry.

The result of the SSF experiment with spruce slurry is shown in FIG. 5. FIG. 5 clearly shows that addition of dithionite and sulphite led to higher ethanol production compared to the untreated hydrolysate. The ethanol formation in the samples with 10 mM dithionite leveled off after about 45 h. The samples with 7.5 mM dithionite reached the same high levels of ethanol, but ethanol formation was slightly slower. Ethanol formation in the samples to which sulphite was added leveled off after 20 h and resulted in a lower ethanol production compared to the samples to which dithionite was added (FIG. 5).

Thus, Example 2 shows that reducing agents may be added to a fermentor in situ, thus providing for chemical in situ detoxification in a SSF process. Consequently, the addition of reducing agents radically improved the fermentability of inhibitory lignocellulose hydrolysates in the SSF process without the need for a separate detoxification step. Dithionite and sulphite were chosen for the SSF process considering their utilization in large-scale industrial processes.

Example 3

Detoxification of Spruce Slurry in a Simultaneous Saccharification and Fermentation (SSF) Process:

Ethanol Yield as a Function of Dithionite and Sulphite Concentrations

Materials and Methods

A spruce slurry was prepared according to Examples 1 and 2 above. Different flasks were filled with 100 g each of the spruce slurry and were subjected to a SSF process according to Example 2 above, but with different amounts of dithionite and sulphite added. The produced ethanol was monitored during the fermentation.

Results

Figure 6:
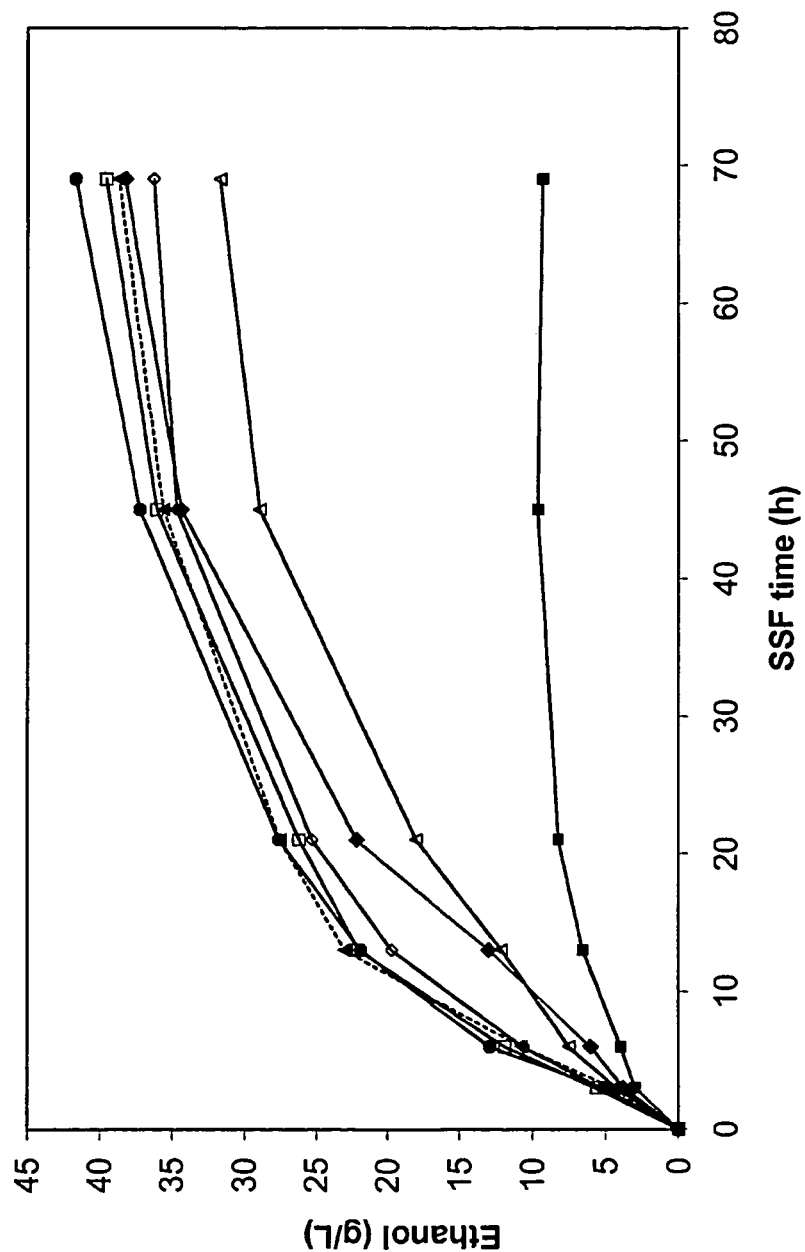
FIG. 6 shows the ethanol production during simultaneous saccharification and fermentation of spruce slurry with addition of different concentrations of dithionite. The data represent: ■, solid line: dithionite treatment (2.5 mM); ♦, solid line: dithionite treatment (5 mM); ▲, dashed line: dithionite treatment (7.5 mM); ●, solid line: dithionite treatment (10 mM); □, solid line: dithionite treatment (15 mM); ◇, solid line: dithionite treatment (20 mM); Δ, solid line: dithionite treatment (30 mM).

Sodium dithionite was added such that the final concentration during fermentation was between 2.5-30 mM. Further, sodium sulphate was added such that the final concentration during fermentation was between 2.5-30 mM. The produced ethanol as a function of time is plotted in FIG. 6 and FIG. 7. It was seen that treatment with 7.5 mM, 10 mM and 15 mM sodium dithionite resulted in the highest ethanol production, but also 5 mM and 20 mM sodium dithionite resulted in high ethanol concentrations, about 35-40 g/L after 70 hours (see FIG. 6). Treatment with 5 mM sodium dithionite resulted in a slower effect but the fermentation reached a final ethanol concentration that was similar to the concentration reached using 7.5 mM. However, treatment with 2.5 mM and 30 mM dithionite resulted in lower final ethanol concentrations, about 30 g/L after 70 hours using 30 mM dithionite and about 10 g/L after 70 hours using 2.5 mM dithionite.

Figure 7:
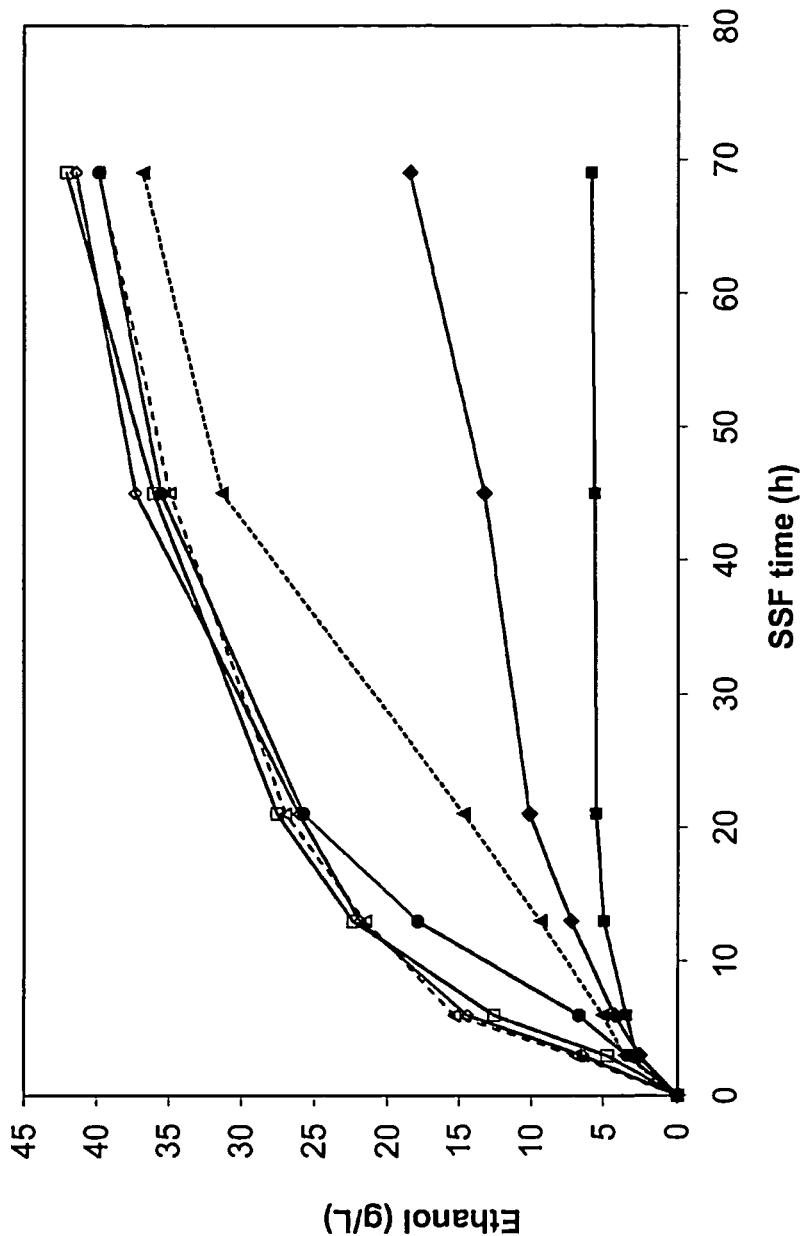
FIG. 7 shows the ethanol production during simultaneous saccharification and fermentation of spruce slurry with addition of different concentrations of sulphite. The data represent: ■, solid line: sulphite treatment (2.5 mM); ♦, solid line: sulphite treatment (5 mM); ▲, dashed line: sulphite treatment (7.5 mM); ●, solid line: sulphite treatment (10 mM); □, solid line: sulphite treatment (15 mM); ◇, solid line: sulphite treatment (20 mM); Δ, dashed line: sulphite treatment (30 mM).

Further, it was seen that treatment with 15 mM, 20 mM and 30 mM sulphite resulted in high ethanol concentrations, about 40 g/L after 70 hours (FIG. 7). Treatment with 7.5 mM and 10 mM sulphite gave a slower effect but resulted in a high final ethanol concentration, about 35-40 g/L. However, treatment with 2.5 mM and 5 mM sulphite did not result in as high final ethanol concentrations compared to treatment with sulphite concentrations above 10 mM.

Consequently, Example 3 shows that in a process of in situ detoxification in a fermentor, higher ethanol concentrations are obtained during fermentation if dithionite is added to a final concentration of 7.5-20 mM compared to if dithionite is added to final concentrations that are outside this range. Further, Example 3 shows that chemical in situ detoxification with sulphite of above 10 mM is more advantageous, i.e. leading to higher ethanol concentrations during fermentation, compared to if sulphite is added to a final concentration of below 10 mM.

Example 4

Detoxification of Spruce Slurry in a Simultaneous Saccharification and Fermentation (SSF) Process:

Ethanol Yield Vs. Time of Addition of Sulphite or Dithionite

Materials and Methods

A spruce slurry was prepared as described in Example 1 above. Fermentation experiments with the yeast *Saccharomyces cerevisiae* were carried out as in the previously described Examples, except that the addition of reducing agent 10 min prior to inoculum was compared with simultaneous addition of reducing agent and inoculum, and addition of reducing agent 45, 105, 240, or 480 min after inoculum. Both sodium dithionite and sodium sulphite were included in the experiments and both were added to 10 mM. The ethanol concentration was determined after 24 hours according to the analysis described in Example 1 above.

Results

Figure 8:
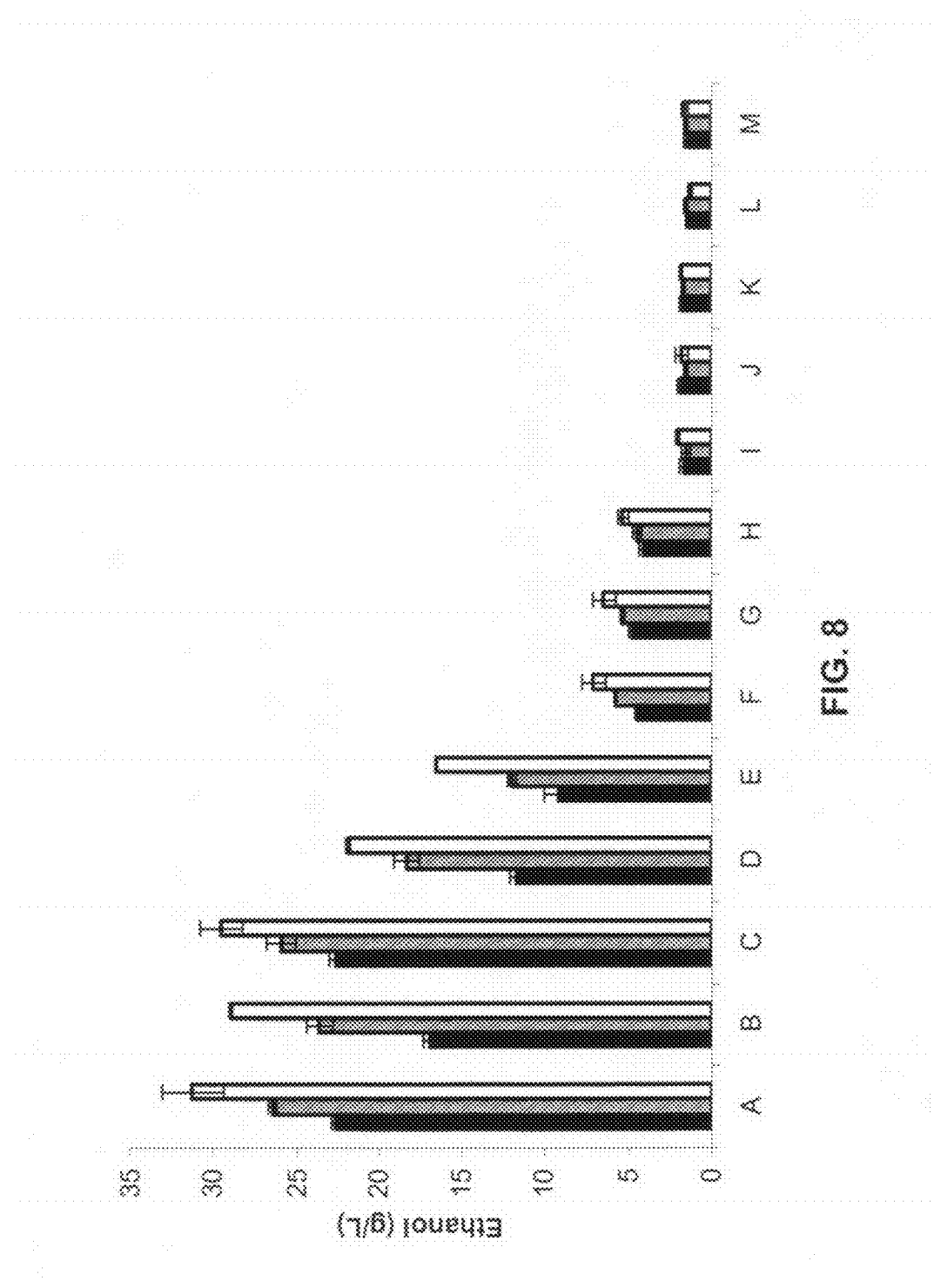
FIG. 8 shows the ethanol production (g/L) after 24 h (black bars), 48 h (grey bars) and 72 h (white bars) of simultaneous saccharification and fermentation of spruce slurry. The data indicate: (A) 10 mM dithionite added 10 min prior to inoculum, (B) 10 mM sulphite added 10 min prior to inoculum, (C) 10 mM dithionite added at the time of inoculum, (D) 10 mM sulphite added at the time of inoculum, (E) 10 mM dithionite added 45 min after inoculum, (F) 10 mM sulphite added 45 min after inoculum, (G) 10 mM dithionite added 105 min after inoculum, (H) 10 mM sulphite added 105 min after inoculum, (I) 10 mM dithionite added 240 min after inoculum, (J) 10 mM sulphite added 240 min after inoculum, (K) 10 mM dithionite added 480 min after inoculum, (L) 10 mM sulphite added 480 min after inoculum, and (M) spruce slurry with no addition of reducing agent. Mean values based on two measurements are presented. Error bars indicate the standard deviations.

The results of the experiments of adding the reducing agents prior to inoculum, adding reducing agents simultaneous with inoculum and adding reducing agents after inoculum are shown in FIG. 8. The results clearly shows that there is no need to add the reducing agent before the fermentation is initiated, since addition after inoculum also resulted in a higher ethanol yield compared to the untreated slurry. Furthermore, addition 45 or 105 min after inoculation also resulted in improved fermentability, while addition after 240 or 480 min had minor positive effects. It was seen that the addition of dithionite resulted in better improvement than the addition of sulphite (FIG. 8).

Consequently, Example 4 demonstrates that a fermentation in which the ethanol production is inhibited may be "rescued" after the fermentation reaction has been initiated by the addition of a reducing agent to the fermentor. However, it appears that in situ addition of a reducing agent before or simultaneous as the fermentation is initiated results in a higher ethanol yield. Also, it should be noted that the specific times used in this lab-scale experiment does not necessarily correspond to an industrial context. Thus additions of reducing agent to the fermentor more than 4 hours after the yeast addition may be efficient in a large scale fermentation.

Example 5

Detoxification of Sugarcane Bagass Slurry in a Simultaneous Saccharification and Fermentation (SSF) Process:

Ethanol Yield as a Function of Dithionite and Sulphite Concentrations

Materials and Methods

SSF experiments were also performed with sugarcane bagass slurries. The sugarcane bagass slurries were prepared as described in Example 1. Reducing agents, dithionite and sulphite, respectively, were added 10 min prior to inoculum in concentrations of studied 7.5 and 10 mM. The ethanol concentration was measured after 13 and 45 hours according to the protocol described in Example 1.

Results

Figure 9:
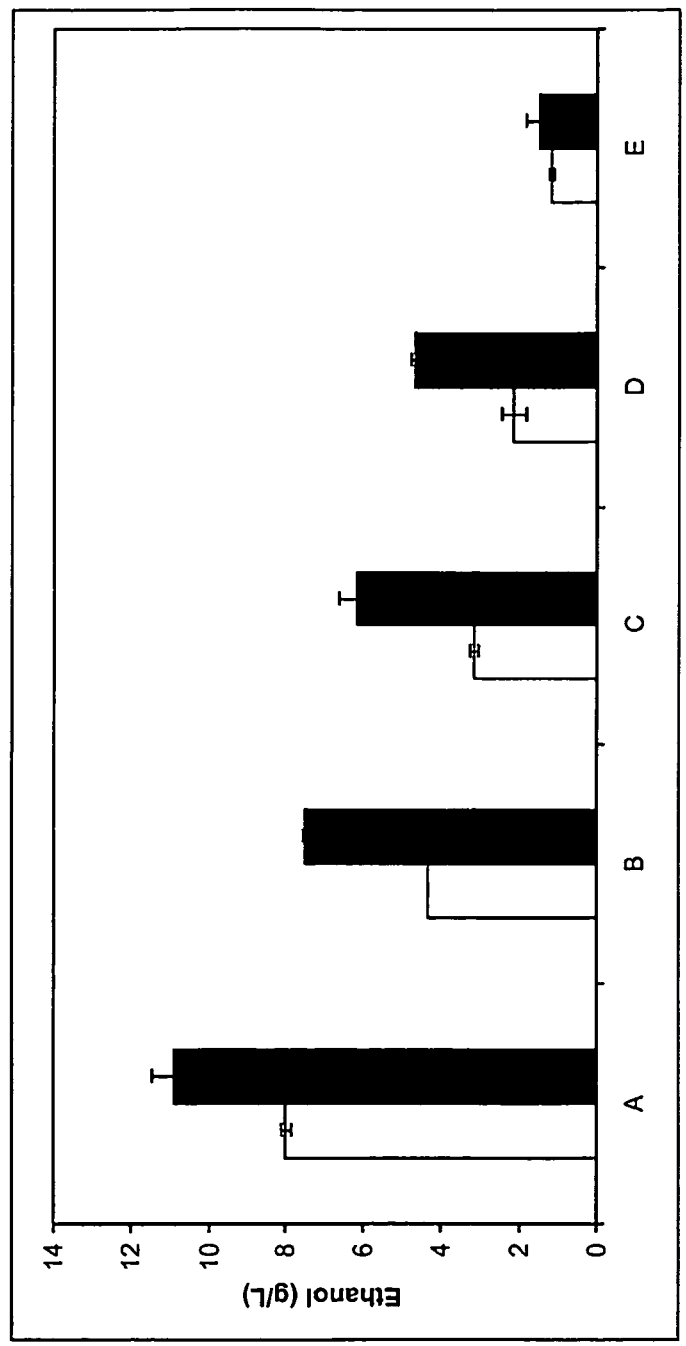
FIG. 9 shows ethanol production (g/L) after 13 (white bars) and 45 (black bars) hours of simultaneous saccharification and fermentation of sugarcane bagass slurry. The data indicate: (A) addition of 10 mM dithionite, (B) addition of 7.5 mM dithionite, (C) addition of 10 mM sulphite, (D) addition of 7.5 mM sulphite, (E) bagass slurry with no reducing agent added. Every bar represents the mean value of two parallel SSF experiments. Error bars indicate the standard deviations.

The results of the addition of reducing agents to SSF of sugarcane bagass slurries are shown in FIG. 9. Both dithionite and sulphite resulted in improved fermentability. Both concentrations of dithionite (10 and 7.5 mM) were better than any of the sulphite concentrations (FIG. 9). Further, it was observed that addition of sulphite or dithionite did not lead to any formation of precipitates. Example 5 thus demonstrates that in situ addition of dithionite results in higher yields of ethanol during fermentation of a sugarcane bagass slurry compared to in situ addition of sulphite, even after 45 hours of fermentation.

Example 6

Control Experiment:

Effect of Sulphite and Dithionite on Saccharide Concentrations of a Hydrolysate Prepared by Acidic Hydrolysis Materials and Methods A dilute-acid spruce hydrolysate was prepared by two-step hydrolysis in a 250-L batch reactor. In the first step, chipped Norway spruce (*Picea abies*) was impregnated with sulfuric acid (0.5% w/v) and treated at 190° C. for 10 min. The liquid and solid fractions were separated by filtration. The solid fraction was washed with water, reimpregnated with sulfuric acid, and loaded into the reactor. In the second hydrolysis step, the material was treated at 215° C. for 10 min. The liquid fraction was recovered by filtration and was pooled with the liquid fraction from the first step. The pooled liquid fractions are referred to as the spruce hydrolysate.

The pH of the spruce hydrolysate was adjusted to 5.5 with $NH_4OH$. Sodium dithionite was added to different samples to concentrations of 2.5, 5, 7.5, 10, 12.5, and 15 mM. The treatments were performed at 21° C. for 5 min with stirring. To compare the efficiency of the treatments with alkaline detoxification, a hydrolysate was treated with $NH_4OH$ at optimal conditions (pH 9, 55° C., 3 h). Analyses of monosaccharides, furan aldehydes and phenolic compounds were performed by using high-performance liquid chromatography (HPLC).

Results

No significant degradation of monosaccharide was noted in the samples treated with sodium dithionite (see Table 4). Further, additions of dithionite led to similar sugar concentrations as the samples subjected to alkaline treatment.

TABLE 4

Concentrations (g/L) of monosaccharides and inhibitors in the spruce hydrolysate prepared by acidic hydrolysis.

| | Glucose | Xylose | Arabinose | Galactose | Mannose | Phenolic compounds | Furfural | HMF |
|---|---|---|---|---|---|---|---|---|
| Untreated hydrolysate | 18.3 | 6.4 | 2.1 | 2.9 | 14.6 | 2.8 | 0.7 | 2.2 |
| Dithionite (2.5 mM) | 18.3 | 6.6 | 2.1 | 2.9 | 14.9 | 2.9 | 0.6 | 2.0 |
| Dithionite (5.0 mM) | 18.7 | 6.6 | 2.0 | 2.9 | 14.7 | 2.9 | 0.6 | 2.0 |
| Dithionite (7.5 mM) | 18.8 | 6.7 | 2.1 | 3.0 | 14.8 | 2.9 | 0.5 | 1.8 |
| Dithionite (10.0 mM) | 18.1 | 6.5 | 2.0 | 3.0 | 14.9 | 2.8 | 0.6 | 1.9 |
| Dithionite (12.5 mM) | 18.1 | 6.4 | 2.0 | 2.9 | 14.7 | 2.9 | 0.6 | 1.9 |
| Dithionite (15.0 mM) | 18.3 | 6.4 | 1.9 | 2.9 | 14.7 | 2.8 | 0.5 | 1.8 |
| $NH_4OH$-detox. | 17.7 | 6.8 | 2.0 | 3.0 | 14.2 | 2.5 | 0.5 | 1.5 |

Abbreviation used:
$NH_4OH$-detox. = ammonium hydroxide detoxification.

Thus, Example 6 shows that treatment of an acidic hydrolysate by means of dithionite additions did not lead to any decrease in sugar concentrations as compared to the untreated hydrolysate. Consequently, the addition of dithionite has no negative effect on the monosaccharide concentrations of hydrolysates prepared by acidic hydrolysis.

Example 7

Addition of Reducing Agent to Hydrolysate Prepared by Acidic Hydrolysis: Effect on Fermentation Materials and Methods A spruce slurry was prepared an subjected to acidic hydrolysis as described in Example 6. The pH of the spruce hydrolysate was adjusted to 5.5 with $NH_4OH$. Sodium dithionite was added to different samples to concentrations of 2.5, 5, 7.5, 10, 12.5, and 15 mM. The treatments were performed at 21° C. for 5 min with stirring. In addition, treatments with 0.1% (7.9 mM) and 1% (79.3 mM) sodium sulphite were performed. To compare the efficiency of the treatments with alkaline detoxification, a hydrolysate was treated with NH$_4$OH at optimal conditions (pH 9, 55° C., 3 h). Furthermore, a sugar solution (glucose 18 g/L, mannose 14 g/L) was prepared to evaluate if the effect of the sodium dithionite treatment was due to an effect on the hydrolysate or the ethanolic fermentation with yeast. Half of the sugar solution was treated with 10 mM sodium dithionite, whereas the rest was left untreated as a reference. The volumes of treated and untreated samples were equalized with water and the pH was adjusted to pH 5.5 prior to the fermentation. Fermentation was performed with the yeast *Saccharomyces cerevisiae* as described in the previous Examples.

Results

Figure 10:
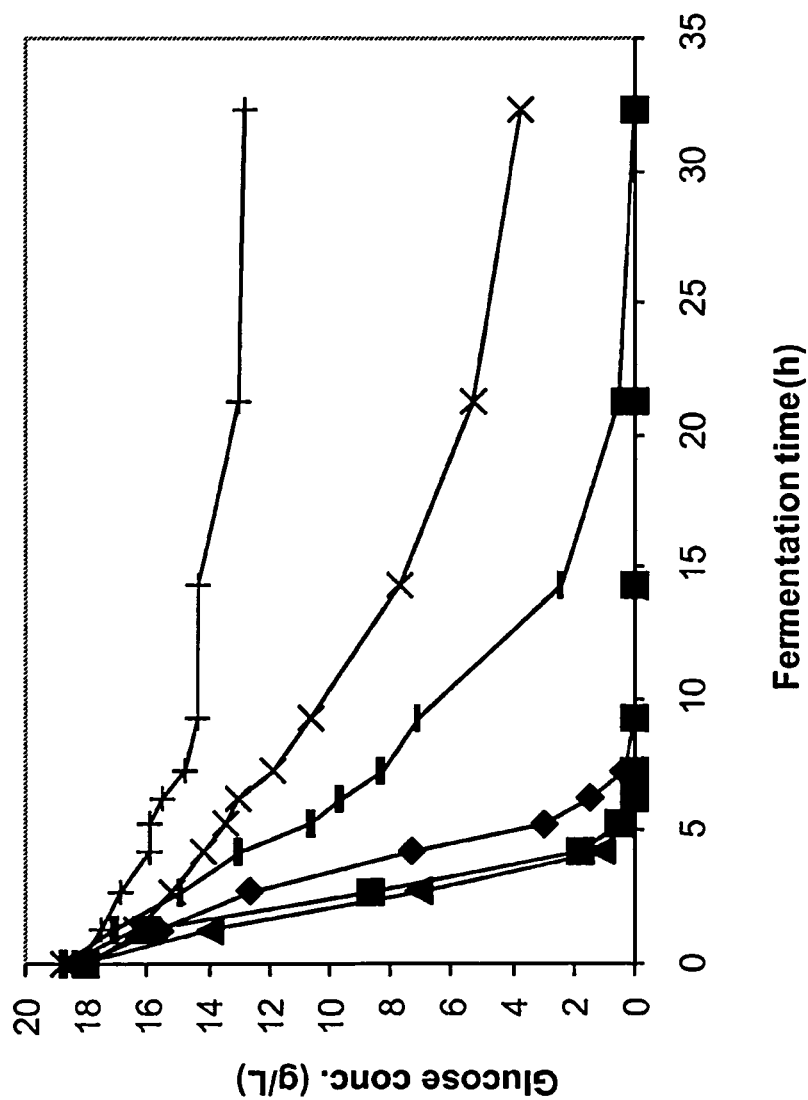
FIG. 10 shows the glucose consumption during fermentation of a spruce hydrolysate prepared from acid hydrolysis after different treatments. +: Sodium dithionite treatment (2.5 mM); ×: Sodium dithionite treatment (5.0 mM); –: Sodium dithionite treatment (7.5 mM); ♦: Sodium dithionite treatment (10.0 mM); ■: Sodium dithionite treatment (12.5 mM); ▲: Sodium dithionite treatment (15 mM).
Figure 11:
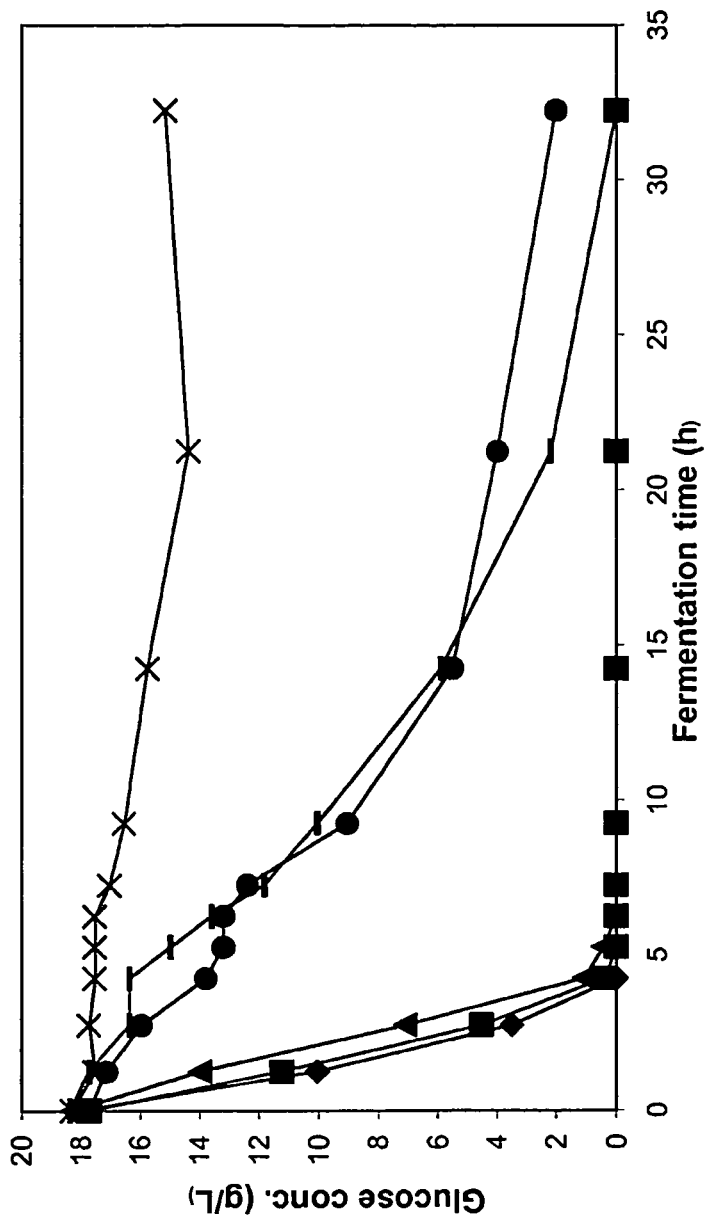
FIG. 11 shows the glucose consumption during fermentation of a spruce hydrolysate prepared from acid hydrolysis after different treatments. ×: Untreated hydrolysate. ●: Sodium sulphite treatment (0.1%); –: Sodium sulphite treatment (1%); ▲: Sodium dithionite treatment (15 mM); ■: NH$_4$OH treatment; ♦: Sugar solution.

The sodium dithionite treatments resulted in improved fermentability of the spruce hydrolysate, with an increased glucose consumption rate when the addition of dithionite was increased from 2.5 mM to 10 mM (FIG. 10). However, treatments with sodium dithionite concentrations of 12.5 mM and higher did not differ much with regard to improvement in fermentability. Further, it was also seen that the glucose consumption rate was increased when sulphite was added to the spruce hydrolysate prepared by acidic hydrolysis. The treatment with 1% sodium sulphite resulted in a better fermentability compared to the untreated hydrolysate (FIG. 11). It was also seen that the sample treated with 15 mM sodium dithionite fermented about as well as the NH$_4$OH treated sample and the plain sugar solution (FIG. 11). The untreated hydrolysate fermented poorly and only minor amounts of glucose were consumed. (FIG. 11). The cell viability during fermentation is displayed in Table 5.

TABLE 5

Cell viability during fermentation.

| | Viable cells (%) Fermentation time | |
|---|---|---|
| | 2.25 h | 7 h |
| Untreated hydrolysate | 82.3 ± 2.5 | 0.0 ± 0.0 |
| Sodium dithionite treatment (10.0 mM) | 91 ± 1.0 | 96.7 ± 2.5 |
| NH$_4$OH treatment | 95.3 ± 3.0 | ND |
| Sugar solution | 86.3 ± 5.4 | ND |
| Sugar solution and sodium dithionite treatment (10 mM) | 80.8 ± 4.5 | 84.3 ± 2.9 |

ND: not determined (the fermentation was finished at that time).

It could be concluded that the cell viability was high in the samples treated with dithionite, and that it remained high after 7 hours of fermentation. The hydrolysate treated with 10 mM dithionite had even a higher cell viability compared to the untreated hydrolysate.

The ethanol concentration, yield and productivity for untreated hydrolysate, hydrolysate treated with dithionite and hydrolysate treated with NH$_4$OH are displayed in Table 6. It was seen that in situ treatment with 15 mM dithionite resulted in higher ethanol concentration, yield and productivity compared to the untreated hydrolysate at all sampled time points after initiation of the fermentation. Further, treatment with dithionite also resulted in higher ethanol concentration, yield and productivity compared to the alkaline treatment.

TABLE 6

Ethanol concentration (g/L), yield (g EtOH/g consumed glucose and mannose) and productivity (g EtOH × L$^{-1}$ × h$^{-1}$) of fermentation of spruce hydrolysates prepared by acidc hydrolysis. The ethanol concentrations are mean values of two measurements. The relative standard deviation of the ethanol analysis was <9%.

| | Ethanol concentration | | | | Yield | | | | Productivity | | | |
|---|---|---|---|---|---|---|---|---|---|---|---|---|
| | 2.75 h | 4.25 h | 6.25 h | 9.25 h | 2.75 h | 4.25 h | 6.25 h | 9.25 h | 2.75 h | 4.25 h | 6.25 h | 9.25 h |
| Untreat. hydro. | 1.00 | 1.11 | 1.64 | 2.03 | 0.14 | 0.34 | 0.29 | 0.22 | 0.36 | 0.26 | 0.26 | 0.22 |
| Dithionite treatment 15.0 mM | 5.07 | 9.81 | 14.59 | 15.47 | 0.37 | 0.44 | 0.47 | 0.49 | 1.84 | 2.31 | 2.33 | 1.67 |
| NH$_4$OH treatment | 4.56 | 10.75 | 9.81 | 14.08 | 0.30 | 0.42 | 0.32 | 0.47 | 1.66 | 2.53 | 1.57 | 1.52 |

Untreat. hydro. = untreated hydrolysate

To summarize, Example 7 showed that:

In situ detoxification of spruce hydrolysate prepared by acidic hydrolysis using reducing agents increased the glucose consumption rate, obtained ethanol concentration, ethanol yield and ethanol productivity.

Treatment with dithionite resulted in a higher percentage of viable cells compared to untreated hydrolysate.

Dithionite appeared to be more effective compared to sulphite as a detoxification agent. Further, treatment with 15 mM was shown to give a higher ethanol concentration, ethanol yield and ethanol productivity compared to alkaline treatment.

Example 8

Detoxification of Model Inhibitor Coniferyl Aldehyde

Materials and Methods

The strongly inhibiting compound coniferyl aldehyde, which is present in lignocellulosic hydrolysates, was selected as a model compound for studies with dithionite. A sugar solution (glucose 18 g/L, mannose 14 g/L) with a coniferyl aldehyde concentration of 2.5 mM was prepared. Half of the solution was treated with 10 mM of sodium dithionite and the rest of the solution was left untreated as a reference. Fermentation was performed with the yeast *Saccharomyces cerevisiae* as described in the previous Examples.

Results

The cell viability in the sugar solution with coniferyl aldehyde and in the sugar solution with coniferyl aldehyde and sodium dithionite treatment are displayed in Table 7. It was seen that the cell viability in the presence of coniferyl aldehyde increased from 1.7% to 76.7% after treatment with dithionite.

TABLE 7

Cell viability during fermentation.

| | Viable cells (%) Fermentation time | |
|---|---|---|
| | 2.25 h | 7 h |
| Sugar solution with coniferyl aldehyde (2.5 mM) | 1.7 ± 1.5 | 0.0 ± 0.0 |
| Sugar solution with coniferyl aldehyde (2.5 mM) and sodium dithionite treatment (10 mM) | 76.7 ± 6.8 | 75 ± 8.0 |

ND: not determined (the fermentation was finished at that time).

Figure 12:
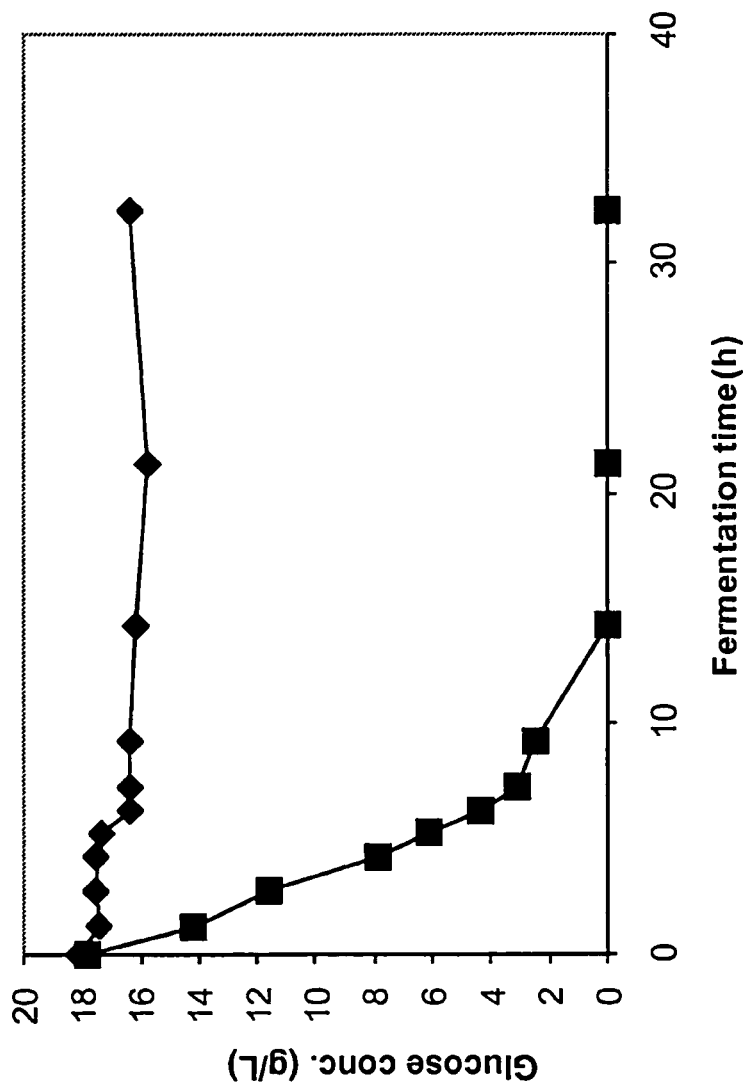
FIG. 12 shows the glucose consumption of a sugar solution with 2.5 mM coniferyl aldehyde. ♦: Sugar solution with coniferyl aldehyde (2.5 mM). ■: Sugar solution with coniferyl aldehyde (2.5 mM) and sodium dithionite treatment (10 mM).

Further, it was also seen that treatment of the coniferyl aldehyde sample resulted in improved fermentability (FIG. 12). Untreated sugar solution with coniferyl aldehyde resulted in approximately no reduced glucose concentration, whereas the glucose consumption rate was much higher after addition of dithionite. Consequently, Example 8 showed that dithionite could detoxify highly toxic samples, such as sugar solutions comprising coniferyl aldehyde Example 9

Detoxification Using DTT, Ascorbic Acid and Glutathione

Materials and Methods

Dithiothreitol (DTT), ascorbic acid, and reduced glutathione were also evaluated as reducing agents for improved fermentability. Spruce hydrolysate samples were prepared as in Example 6.

Two samples were treated with DTT to 2 and 20 mM, respectively, two samples were treated with ascorbic acid to 10 and 100 mM, respectively and two samples were treated with glutathione to 1 and 10 mM, respectively.

The treatment time was 3 h for all samples and fermentation was performed as described in the previous Examples.

Results

Figure 13:
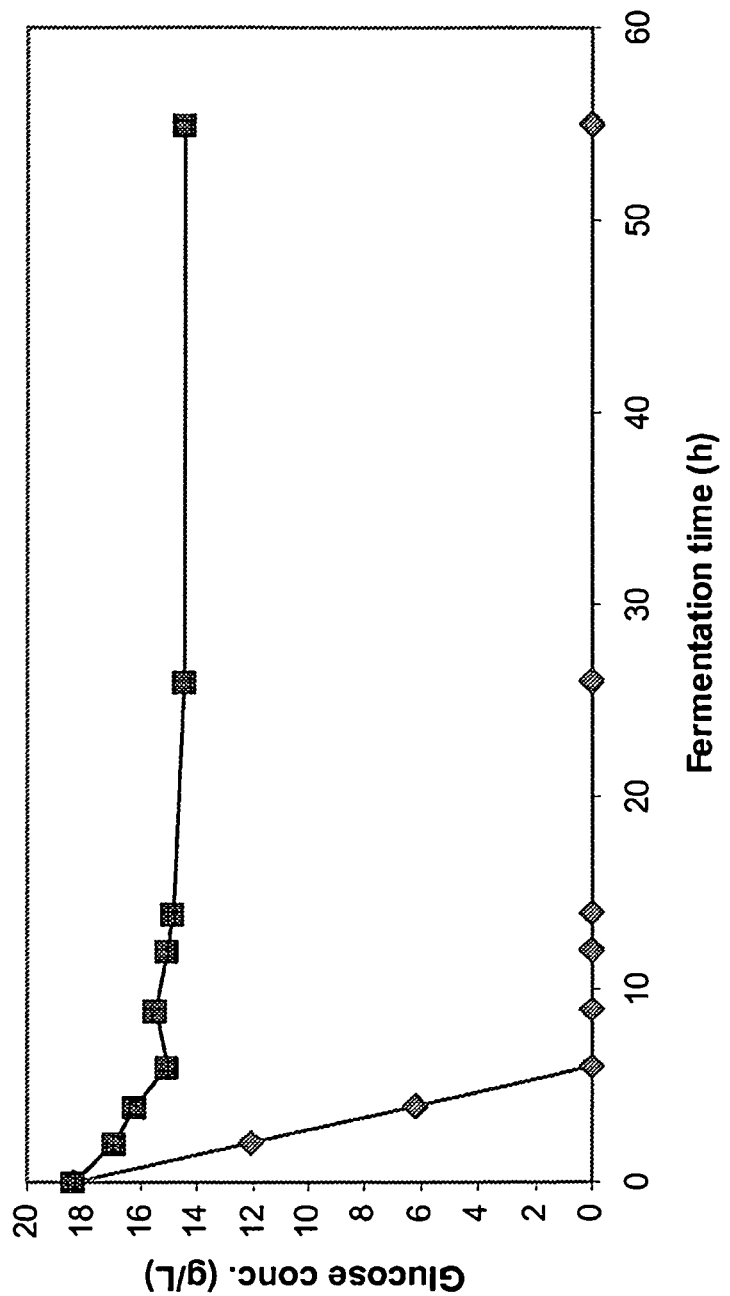
FIG. 13 shows the glucose consumption of a during fermentation of a spruce hydrolysate prepared by acid hydrolysis after treatment with DTT (dithiothreitol). ■: Untreated hydrolysate; (♦): treatment with 20 mM DTT.

The experiments with DTT, ascorbic acid and glutathione resulted in improved fermentability when the highest concentrations were used (i.e. 20 mM DTT; 100 mM ascorbic acid; or 10 mM glutathione). The glucose consumption during fermentation after treatment with 20 mm DDT is shown in FIG. 13. It was clearly seen that the treatment of 20 mM DTT resulted in a higher glucose consumption rate compared with the untreated sample.

Thus, Example 9 shows that chemical in situ detoxification of spruce hydrolysates prepared by acidic hydrolysis could be performed with the reducing agents DTT, ascorbic acid and glutathione.

The invention claimed is:

1. A method of increasing the fermentability of a process of producing ethanol, butanol, or succinic acid by fermenting pretreated lignocellulose material, that contains fermentation inhibitors, comprising the steps of
   a) measuring the fermentability of an ongoing yeast fermentation process and if said fermentability is below a reference value indicating decreased production, then
   b) adding dithionite to the ongoing fermentation process.

2. The method according to claim 1, wherein step b) further comprises adding additional yeast to said ongoing fermentation process.

3. The method according to claim 1, wherein the dithionite is added to a material having a temperature of 28-38° C.

4. The method according to claim 1, wherein the dithionite is added to a material having a pH of 3-7.

5. The method according to claim 1, wherein the material to which the dithionite is added has a suspended solids content of at least 5% (w/w).

* * * * *